US006489462B1

(12) United States Patent
Olszewski et al.

(10) Patent No.: US 6,489,462 B1
(45) Date of Patent: *Dec. 3, 2002

(54) SUGARCANE BACILLIFORM VIRUS PROMOTER

(75) Inventors: Neil Olszewski, Roseville, MN (US); Iris Tzafrir, Stillwater, OK (US); David A. Somers, Roseville, MN (US); Benham Lockhart; Kimberly A. Torbert, both of St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/502,831

(22) Filed: Feb. 11, 2000

Related U.S. Application Data

(60) Continuation of application No. PCT/IB97/01338, filed on Aug. 13, 1997, and a continuation-in-part of application No. 09/349,546, filed on Jul. 8, 1999, now Pat. No. 6,093,569, which is a division of application No. 08/694,869, filed on Aug. 9, 1996, now Pat. No. 5,994,123.

(51) Int. Cl.[7] .......................... A01H 1/00; C07H 21/04; C12N 5/14; C12N 15/00
(52) U.S. Cl. .......................... 536/24.1; 435/6; 435/410; 435/419; 435/320.1; 536/23.1; 536/24.3; 536/24.33; 800/278; 800/295
(58) Field of Search .......................... 435/6, 410, 419, 435/320.1; 536/23.1, 24.1, 24.3, 24.33; 800/278, 295

(56) References Cited

U.S. PATENT DOCUMENTS

| | | | |
|---|---|---|---|
| 5,097,025 A | 3/1992 | Benfey et al. | 536/27 |
| 5,164,316 A | 11/1992 | McPherson et al. | 435/240.4 |
| 5,304,730 A | 4/1994 | Lawson et al. | 800/205 |
| 5,352,605 A | 10/1994 | Fraley et al. | 435/240.4 |
| 5,359,142 A | 10/1994 | McPherson et al. | 800/205 |
| 5,378,619 A | 1/1995 | Rogers | 435/172.3 |
| 5,824,857 A | 10/1998 | Beachy et al. | 800/205 |
| 5,994,123 A | 11/1999 | Olszewski et al. | 435/320.1 |

FOREIGN PATENT DOCUMENTS

| | | | |
|---|---|---|---|
| AU | 60867/90 | 3/1991 | C12N/15/34 |
| DE | 4306832 | 2/1994 | C12N/15/82 |
| WO | 96/06932 | 3/1996 | C12N/15/11 |
| WO | 96/07313 | 3/1996 | A01H/1/04 |

OTHER PUBLICATIONS

"Sugarcane Bacillifrom Virus ORF 1, 2, and 3 DNA, complete cds.", *Genbank*, Accession No., M89923, 4 pgs., (Mar. 1993).

Bhattacharyya–Pakras, et al., "Specificity of a Promoter from the Rice Tungro Bacilliform Virus for Expression in Phloem Tissues", *The Plant Journal*, 4 (*1*), pp. 71–79, (1993).

Bouhida, M., et al., "An Analysis of the Complete Sequence of a Sugarcane Bacilliform Virus Genome Infectious to Banana and Rice", *Journal of General Virology*, 74, pp. 15–22, (1993).

Chen, G., et al., "Rice Tungro Bacilliform Virus: Transcription and Translation in Protoplasts", *Virology*, 204 (*1*), pp. 91–100, (Oct. 1994).

Lockhart, B.E., et al., "Occurence in Sugarcane of a Bacilliform Virus Related Serologically to Banana Streak Virus", *Plant Disease*, 72 (*3*), pp. 230–232, (Mar. 1988).

Medberry, S.L., et al., "Identification of cis Elements Involved in Commelina Yellow Mottle Virus Promoter Activity", *The Plant Journal*, 3 (*4*), pp. 619–626, (1993).

Medberry, S.L., et al., "The Commelina Yellow Mottle Virus Promoter is a Strong Promoter in Vascular and Reproductive Tissues", *The Plant Cell*, 4, pp. 185–192, (Feb. 1992).

Torbert, K.A., et al., "Use of Paromomycin as a Selective Agent for Oat Transformation", *Plant Cell Reports*, 14, pp. 635–640, (1995).

Yin, Y., et al., "The Regulatory Regions of the Rice Baciliform Virus Promoter and Interacting Nuclear Factors in Rice (Oryza sativa L.)", *The Plant Jouranl*, 7 (*6*), pp. 969–980, (1995).

*Primary Examiner*—Phuong T. Bui
(74) *Attorney, Agent, or Firm*—Schwegman, Lundberg, Woessner & Kluth, P.A.

(57) ABSTRACT

An isolated and purified DNA molecule comprising a sugarcane bacilliform virus promoter and expression cassettes comprising said promoter are provided. Also provided is a method of using a sugarcane bacilliform virus promoter to express proteins, RNA transcripts, or mixtures thereof, in transgenic plants.

14 Claims, 10 Drawing Sheets

MTQRVRGTGSSTITEDGALLDHQIRDYRRAQHAKHEAQRIAGQA
LAFLRVTSDDPREKTLEMLMQPDVELTRSMKKRARAFPAEVLYGPRSDDIHHKVFQGS
SSQDILLIDDNQLDMTFIKEETFEQLEQAGLRYIHPGILAVRIQPLHPDWSGKLVFIV
FRDIRDNPPRVLGAMEIDLSKGPQMVYINSFMTTIKDFFHGIQLTVKVKGYEGWQGE
ANLHIERLITARLSNTTNVYFKYKVEGVASFIKTKGIKAIEATKKSVKGIRGGEWNIL
PSKLEVVMQPTKVQTTENYDGTTSFRFTNYEGASSSKPVEHNSDDEAYMALFEEEEE
DDITFLNRILSKYSTQQKVVGEEEFSPEEDQIISDFLGKTEEAYPAEIEEEYPALRRL
EQLMKTKVVVQEIEEPSQPVEAKMSTSTGSSAMIPANMDMDGNMPGYAPAQEARGWDS
GETSRRNYGGHSRKWKDESQFFNLPSAMATSGAMLVLTMGNYAKEFDRWQSINTNLLA
SQTFENAEDKITRIENLLGETEKLMFQTWRMAFPTAFEAMKTQATGTNGTQNVFSQMK
RILLGEVPEQGTTNTQDAAYKRIKSLVCQEMTYPAIMRYLVGYRNLAARSGRAWVNNE
LTDEFFTKLPGKLGDRVKEAFKKYPGVERHVPAATRFTYDYLEICTENNFQKQLRS
LNFCKGFPVVNPVGTRKYGKKYGTRKARSYRGKPHKSHVRIEKKYLQQREKKCRCYV
CGSPDHLMKDCKSPMKRQERVNLANELDIPDGYDLVSVGYDESDIDEIYSVSENEECQ
AHLGLNEDEQLPKVPQTFEEWEYYKDEFIMMADIEESENSDEEKGPFLVGPKGGFRH
QMEVSYKQYKCEHDWDFTRTRVKPCKRCLKTVTKGQYIYCRTCKITVCHECSEFCYNI
KIEGAEAVKPPEKKSNYELLAKQLLIENSKLKMEKEILIEELNKEIKAHQETKKGKEL
YIEEASTEVENEIETWKSRAELFEALYNEEVKKNKASTSSVTEGMYQVQIDHLRKELR
EVEATLEVNKVEESEEEAEEVMMASAVKDEMYRFPVIIEVPEVGKVQLTALLDTGATR

FIG. 1A

SCINQVFIEEKFLQPTKFKVKIHGVNSVTKLDRQVKDGAKLWAGENWFRLPITYVGPM
YMGEKTQMLIGCNFMQSLAGGVRLEGRTVTFYKYIASIKANEYLQAEAEEILVATSEQ
EFINRSFMSKNKRLLEEMKEQGYMGEDTLAHWNKNQIKCKIELRNPDLIIKDKPQTLL
NIQKKEAMRKHIDALLERKVIRPSKSPHRTNAFIVESGTSIDPKTGKEIRGKPRLVFN
YKRLNDNTWPDQYSLPGINALLKNVARAKIFSKFDLKSGFHQVAMDEESIPLTAFSAY
NELYEWLVMPFGLKNAPAIFQRKMDQCFRGTEGFIAVYIDDILVFSEDEEQHAEHLWK
MLQICKRNGLILSPSKYKIGVKKVDFLGSTIGDNQLAVQEHIIKKIAEFDDEKLKTKE
GLKSWLATLNYARNHIKDMGKLLGPLYPKTSEKGERRLNSEDWKLINRIKTMVRTLPN
LTIPPEDAYIIIETDACATGWGAVCKWKKNKADPRNTEQICRYASGKFDKPKGTCDAE
IYGVMNGLEKMRLFYLDKREITVRTDSSAIERFYNKSAEHKPSEIRWIRFMDYITGAG
PEIVIEHIKGKSNGLADILSRLKAKLAQNEPTEEMILLTQAIREVIPYPDHPYTEQLR
EWGNKILDPFPTFKKDMFERTEQAFMLTEEPVLLCACRKPAIQLVSRTSANPGRKFFK
CAMNKCHCWYWADLIEEHIQDRIDEFLKNLEVLKTGGVQTMEEELMKEVTKLKIEEQE
FEEYQATPRAMSPVAAEDVLDLQDVSNDD

FIG. 1B

```
   1 tggtatcaga gcgaggtatg atttctgtat ccgctatgtt ctaaatttct tagataaggg
  61 gccaaggct ctgctgatga gtttaaggac aactacttgt gcaagttaca tagcatgata
 121 cgtcgaaagg ctgaaaatat ccaaaatact gtctattgtt tggaaaacta ggttgttcta
 181 ggggagaacg ttaatgaggg gtaagcttag ttcattctga aaatcaaggt ctgtgattgt
 241 agttgagctc agtaattaag tgctgaagga agtaagatct aggtaggaca aaagtacccg
 301 tcaaggcagg aggccgctaa ggggaaaaga gccagacgat caaagctttt tcagcacggt
 361 tgttgagttt agctatcaag aaatagcctt gagactaaga ttcatcacta agaactgcct
 421 actcaagcct ccctgaatcc gcctattagt acaaacgaga caacagtata aggagaaact
 481 atatgcctgt aagacttaag tgcaaaagta acctctggaa ctgggtagaa gtctagagac
 541 tctgaaagca tcccaaggta tccccttatct ccattagaac actgtgatac agttcttgta
 601 tctacctttgc atgaaatctg aagccgagtg ggaaacacag tttaccgctt ggaagaattc
 661 ccatatattc gaaaacgcta accaagagct tattcttgga acaaagatct ctaattctga
 721 tttaaatcat aatctgcgta ctacttgcta tagagtagat cttggataca aagttctgct
 781 aacctcgcag cagaaggcgt tcgagcacag gaaggagcta ttctctgaag ggagaaagca
 841 ccttgctgat caaagcagga agctacaact cgtagctgac aaagcggaac aatcgctgat
 901 cattcagaag gaacagcgtg cacgtctgaa gaaggttgaa gacggcctat cgaccctcag
 961 taggagatc cacgaccttc gtgtggaata cctgaagcgg aggcctttat caaaagaaga
1021 cgttgctgaa cttgtgctga caatctcaga gcagcccaag cttatcgaga agcagaccga
1081 gttgctcctc gagcaggtca agaagctggt ggagaccaca cgtagagaag ttgagacggt
1141 tcaccacatg gtgaaacgta gtcagctgatg agtatcaacg aaccagcata cgcaaaggct
1201 ctcgagaaga ccaagaatat cctggagag ttaaccattg gcttcgttgc aggaaacgca
1261 agcatcacaa cgcttaccaa gcagaataac caagacttga agtactgct tacctgcac
1321 ggaaagatca gtctttgga ggacaaaatc caagacttga aggaagacct taccaagaag
1381 gcggacaagc ccagctcatc cgggctagac agcacctgtc acgacctcgc caagaggatc
1441 gaagggttga ggacaggagc agcaccgtg aaggtagttg aaaggggggaa gctaaaagtt
1501 cacgctaatc cctttgaact cctgaggaag atccaatgac gcaaagagtc agaggtaccg
1561 gctccagtac catcacagaa gatggagcac tcttggatca ccagatccga gattacagaa
1621 gagcccagca tgcaaaacat gaggctcaga gaatcgcagg tcaagcactt gcttttctac
1681 gggttacctc agacgacccg agagagaaga ccctggagat gctcatgcag cctgatgtgg
```

FIG. 2A

```
1741  agctaaccag  gagcatgaag  aagagagcca  gagctttccc  agcagaagtt  agcagagaag  ctgtatgcc
1801  caagaagtga  tgatattcat  cacaaagtct  ttcaaggag  ctctagccag  gatatccc
1861  tgattgatga  caatcagctt  gatatgacct  ttatcaagga  ggaaacattc  gagcaattgg
1921  agcaggcagg  actccggtat  attcatcccg  gaatactagc  tgttagaata  cagcctctgc
1981  atccagactg  gtcaggaaaa  ctggttttca  tagttttccg  tgacatcaga  gataaccac
2041  caagagtact  tggagctatg  gaaattgatc  tgagcaaagg  accacaaatg  gtctatgtga
2101  tcaatagctt  catgacaacg  ataaaggatt  tctttcatgg  aatccagctt  actgtcaags
2161  tgaagggtta  tgaaggtttgg  caaggagagg  ccaacttaca  cattgaaagg  ttgataactg
2221  caagattgtc  aaatacaacc  aatgtgtatt  tcaagtataa  ggttgaagga  gtggcgtctt
2281  ttatcaagac  caaaggtata  aaagctattg  aagccactaa  tcaagtataa  aagggcatca
2341  gaggagaga  atggaacatt  ctcccatcaa  agctagaggt  agtcatgcaa  cctaccaagg
2401  tgcagactac  agaaaattat  gatgcacaa  catccttcag  attcacaaat  tatgaaggtg
2461  ccagttcttc  aaagccagta  gagcacaaact  cagatgatga  ggcatatatg  gcgctctttg
2521  aagaagaaga  ggaagaggat  gacatcactt  tcctcaaccg  aatcttatca  aagtactcta
2581  cgcagcaaaa  ggtagtggga  gaagaagaat  tttccccaga  agagaccag  attatttctg
2641  atttctttgg  aaaaactgaa  gaagcctacc  ctgctgaaat  tgaagaagag  tacccagcgc
2701  taagaagact  tgaacaactc  atgaaaacaa  aagttgttgt  tcaagagatt  gaagagccat
2761  cccagccagt  tgaagctaag  atgagtacaa  gcactgatc  atctgctatg  atccctgcaa
2821  acatggacat  ggatggaaac  atgcctggct  atgcaccagc  acaagaagc  agaggatggg
2881  attcaggaga  gactagcaga  agaaactatg  gtggacattc  tagaaaatgg  aaggatgaaa
2941  gtcagttctt  taatcttcca  tctgccatgg  caacatctgg  agcgatgcta  gttctcacaa
3001  tgggaaatta  tgcaaaggag  tttgatagat  ggcagtctat  caacacaaat  ttattagcat
3061  cccagacatt  tgagaatgca  gaagacaaga  tcaccaggat  tgagaatctt  cttggtgaaa
3121  cagaaaagct  aatgttccag  acctggagaa  tggcccttccc  aacggccttt  gaagcaatga
3181  aaactcaagc  cacagaaaca  aatgaaaca  caaagaacac  ctcacaaatg  aagaggatat
3241  tgcttggaga  ggttcctgaa  caaggaacaa  gaaatgacat  atccagcaat  tacaagagga
3301  taaaatctct  tgtctgccaa  gaaatgacat  atgagatat  catgagtta  ctagttggat
3361  atagaaattt  ggctgccaga  tcaggaagag  cttgggttaa  caatgagttc  actgatgaat
3421  tcttcaccaa  gctaccagga  aaattaggag  acgggtaaa  agaagctttc  aagaagaagt
```

FIG. 2B

```
3481 atcccggagt tgaaggcat gtcccagcgg ccacaagatt tacatatgat tacctggaag
3541 aaatttgtac agaaaacaac ttccagaaagc aactcagaag cctgaatttc tgcaaaggct
3601 tcccagtggt caatcctgtt ggaacaagga aaatatggaa gaaatatggg acaagaaaag
3661 caagatctta cagaggcaag ccacacaagt ctcatgtaag aatagagaag aagaaatatc
3721 tgcagcaaag agagaagaaa tgcagatgct atgtctgtgg ttcaccagat cacctgatgg
3781 aggactgcaa aagtcctatg aagagacaag aaagggtgaa cttggcaaat gaattggatg
3841 tcccagatgg ctatgaccta gtctctgttg gatatgatga atcagacatc gatgaaatct
3901 attcagtatc agaaaatgaa gaatgtcagg cacatctagg cctgaatgaa gatgaacagc
3961 taccaaaggt tcctcaaacc tttgaagaat gggaagagta ctacaaagat gagttcatca
4021 tgatgctga tattgaagaa agtgagaaga cagatgaaga aaagggtccg ttccttgtag
4081 gaccaaaagg aggtttcagg caccaaaatgg aagtctcata caagcaatac aagtgtgagc
4141 atgattggga ttttacaaga acaagggtaa aaccttgcaa aagatgcctg aagacagtga
4201 caaaggggca gtacatatac tgcaggacat gcaagatcac agtttgtcat gaatgctcag
4261 aattctgcta caatatcaaa atcgaggag cagaagcagt caagcccca gaaaagaagt
4321 caaactatga gctgctggcc aaacagttgc tgattgaaaa tagcaagctc aaaatggaga
4381 aagagattct tattgaagaa ctcaacaagg aaataaaagc tcatcaagaa acaagagaaa
4441 gaaaagagct ttacattgaa gaagcttcca cggaggtgga aaatgaaatt gaaacatgga
4501 agagtagggc agaattgttt gaagccctat acaatgaaga agtaaaagaa aataaaagcca
4561 gtacatccag tgtgacagaa gggatgtacc aagtccagat cgaccaccta agaaaagaac
4621 tcagggcagg tgaggcaacc cttgaggtaa acaaggtcga agaatctgaa gaagaagctg
4681 aagaagtgat gatggcttca gcagttgctca atgagatgta cagattccca gtgatcatag
4741 aagttccaga agttggaaag gtacaactca cagctctctt ggatacaggt gcaacaaggt
4801 cctgtatcaa ccaagtattc attgaagaga agttttctcca accacgaag ttcaaagtca
4861 agatacatgg ggtaaactca gtaaccgaca ttgaccgaca agtcaaagat ggtgcaaagc
4921 tttgggcagg agaaaattgg ttcagactcc cgatcacata tgttggacca atgtacatgg
4981 gagaaagac gcagatgctc ataggatgca attttatgca atcccttagca ggaggagttc
5041 ggctgaagg aagaacagtg agttctctaca aatacattgc cagtattaag gcaaatgagt
5101 acttgcaagc cgaagcagag gaaattcttg ttgctacctc agaacaagaa tttatcaaca
5161 gaagtttcat gagcaagaac aagaggcttc ttgaggagat gaaggagcaa ggatatatgg
```

FIG. 2C

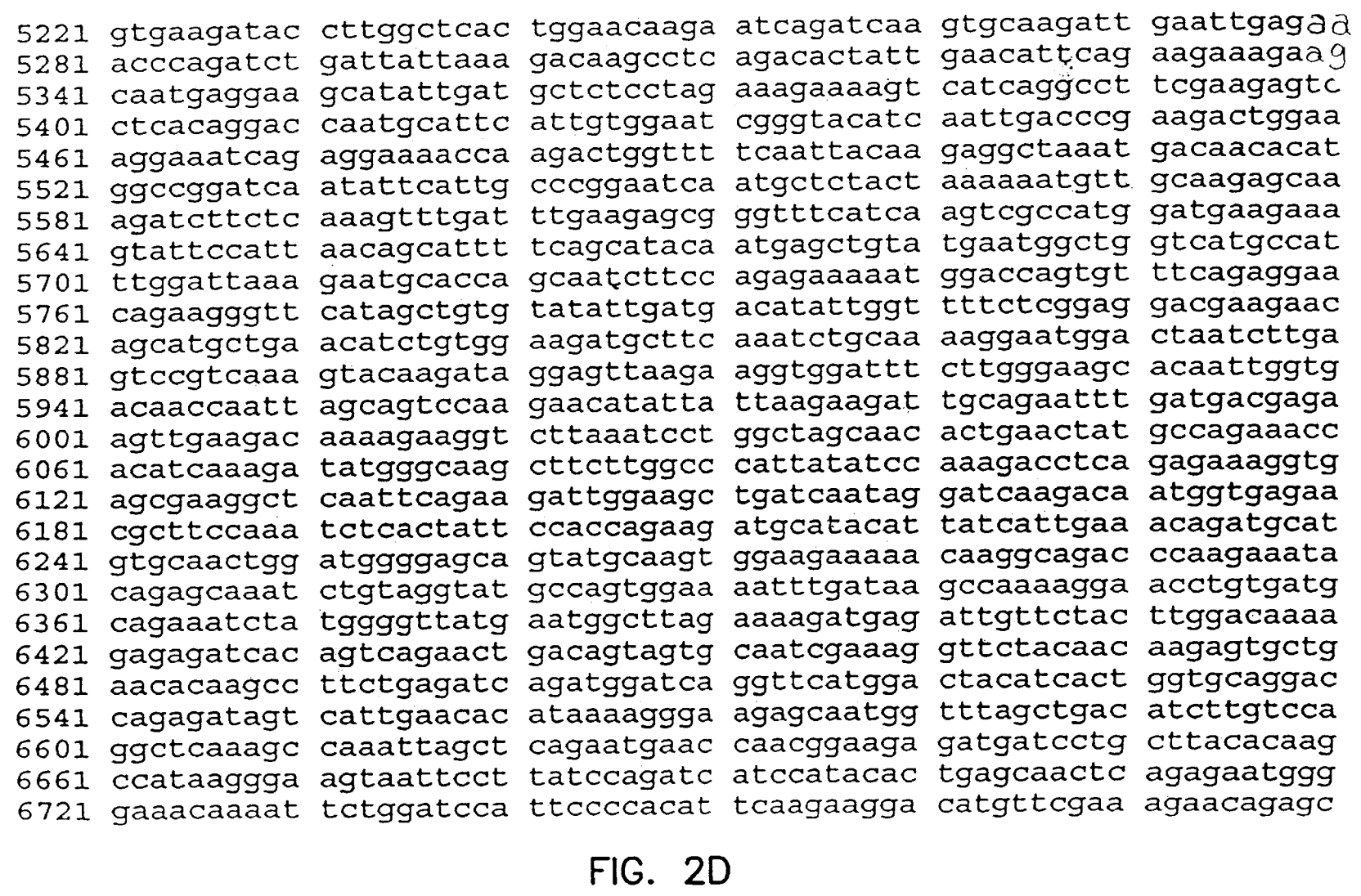

```
5221 gtgaagatac cttggctcac tggaacaaga atcagatcaa gtgcaagatt gaattgagaa
5281 acccagatct gattattaaa gacaagcctc agacactatt gaacattcag aagaaagaag
5341 caatgaggaa gcatattgat gctctcctag aaagaaaagt catcaggcct tcgaagagtc
5401 ctcacaggac caatgcattc attgtggaat cgggtacatc aattgacccg aagactggaa
5461 aggaaatcag aggaaaacca agactggttt tcaattacaa gaggctaaat gacaacacat
5521 ggccggatca atattcattg cccgaatca atgctctact aaaaaatgtt gcaagagcaa
5581 agatctttctc aaagtttgat ttgaagagcg ggtttcatca agtcgccatg gatgaagaaa
5641 gtattccatt aacagcattt tcagcataca atgagctgta tgaatggctg gtcatgccat
5701 ttggattaaa gaatgcacca gcaatcttcc agagaaaaat ggaccagtgt ttcagaggaa
5761 cagaagggtt catagctgtg tatattggt acatattggt tttctcggag gacgaagaac
5821 agcatgctga acatctgtgg aagatgcttc aaatctgcaa aaggaatgga ctaatcttga
5881 gtccgtcaaa gtacaagata ggagttaaga aggtggattt cttgggaagc acaattggtg
5941 acaaccaatt agcagtccaa gaacatatta ttaagaagat tgcagaattt gatgacgaga
6001 agttgaagac aaaagaaggt cttaaatcct ggctagcaac actgaactat gccagaaacc
6061 acatcaaaga tatgggcaag cttcttggcc cattatatcc aaagacctca gagaaaggtg
6121 agcgaaggct caattcagaa gattggaagc tgatcaataag gatcaagaca atggtgagaa
6181 cgcttccaaa tctcactatt ccaccagaag atgcataaat tatcattgaa acagatgcat
6241 gtgcaactgg atggggagca gtatgcaagt ggaagaaaaa caaggcagac ccaagaaata
6301 cagagcaaat ctgtaggtat gccagtggaa aatttgataa gccaaaagga acctgtgatg
6361 cagaaatcta tgggttatg aatggcttag aaaagatgag attgttcttac ttgacaaaa
6421 gagagatcac agtcagaact gacagtagtg caatcgaaag gttctacaac aagagtgctg
6481 aacacaagcc ttctgagatc gacagtgatca ggttcatgga ctacatcact ggtgcaggac
6541 cagagatagt cattgaacac caaatttcct agagcaatgg agagcaagga tttagctgac atcttgtcca
6601 ggctcaaagc caaattagct cagaatgaac aacggaaga tgatcctg cttacacaag
6661 ccataaggga agtaattcct tatccagatc atccatacac agatgatctg agagaatggg
6721 gaaacaaaat tctggatcca ttcccacat tcaagaagga catgttcgaa agaacagagc
```

FIG. 2D

```
6781  aagctttat gctaacagag gaaccagttc tactctgtgc atgcaggaag cctgcaattc
6841  agttagtgtc cagaacatct gccaacccag gaaggaaatt cttcaagtgc gcaatgaaca
6901  aatgccattg ctggtactgg gcagatctca ttgaagaaca cattcaagac agaattgatg
6961  aattctcaa gaatcttgaa gttctgaaga ccggtggcgt gcaaacaatg gaggaggaac
7021  ttatgaagga agtcaccaag ctgaagatag aagagcagga gttcgaggaa taccaggcca
7081  caccaagggc tatgtcgcca gtagccgcag aagatgtgct agatctccaa gacgtaagca
7141  atgacgattg aggagcatt gacgtcaggg atgaccgcag cggagagtac tgggcccatt
7201  cagtggatgc tccactgagt tgtattattg tgtgctttc ggacaagtgt gctgtccact
7261  ttcttttgc acctgtgcca ctttattcct tgtctgccac gatgcctttg cttagcttgt
7321  aagcaaggat cgcagtgcgt gtgtgacacc accccttc cgacgctctg cctatataag
7381  gcaccgtctg taagctctta cgatcatcgg tagttcacca catgatcatt tgagcaagtt
7441  tgcttgaata aagaactat cattccgcat acctgatcct atagtcctag cttgagaaca
7501  agagcgaagt ctatagttga gatcctaaga gaaactcgag gtttttcggg tttcctgggc
7561  gcgttccc
```

FIG. 2E

SUGARCANE BACILLIFORM VIRUS PROMOTER

CROSS-REFERENCE TO RELATED APPLICATIONS

This application is a continuation of International Application No. PCT/IB97/01338, filed Aug. 13, 1997, and a continuation-in-part of U.S. application Ser. No. 09/349,546, filed Jul. 8, 1999, now U.S. Pat. No. 6,093,569, which is a divisional of U.S. application Ser. No. 08/694,869, filed Aug. 9, 1996, now U.S. Pat. No. 5,994,123.

BACKGROUND OF THE INVENTION

One of the primary goals of plant genetic engineering is to obtain plants having improved characteristics or traits. These characteristics or traits include virus resistance, insect resistance, herbicide resistance, enhanced stability and improved nutritional value, to name a few. Recent advances in genetic engineering have enabled the incorporation of preselected genes into plant cells to impart the desired qualities to the plant of choice. The introduced gene, i.e., "transgene," is then expressed in the cells of the regenerated plant, so that the plant will exhibit the trait or characteristic encoded by the transgene.

To express a transgene in a plant cell, the proper regulatory signals must be present and in the proper location with respect to the transgene. These regulatory signals generally include a promoter region, a 5' non-translated leader sequence and a 3' polyadenylation sequence. The promoter region influences the rate at which the RNA product of the transgene, and resultant protein product of the transgene, is made. Promoter activity also can depend on the presence of several other cis-acting regulatory elements which, in conjunction with cellular factors, determine strength, specificity, and transcription initiation site (for a review, see Zawel and Reinberg, *Curr. Opin. Cell Biol.*, 4, 488 (1992)). Strong promoters are able to direct RNA synthesis at a higher rate relative to weak promoters. Constituitive promoters direct RNA production in many or all cell types.

The cauliflower mosaic virus 35S promoter (CaMV35S) is a strong, constitutive promoter in plants (Odell et al., *Nature*, 313, 810 (1985); Jensen et al., *Nature*, 321, 669 (1986); Jefferson et al., *EMBO J.*, 6, 3901 (1987); Kay et al., *Science*, 236, 1299 (1987); Sanders et al., *Nucl. Acids Res.*, 4, 1543 (1987)). This had been shown by detecting substantial levels of reporter gene proteins or mRNAs in extracts prepared from the leaves, stems, roots and flowers of transgenic plants. As a result, the CaMV35S promoter is widely used in the field of plant genetic engineering. Although the CaMV35S promoter appears to be a strong, constitutive promoter in assays involving cell extracts, detailed histological analysis of reporter gene products detectable at the cell and tissue level shows a rather high degree of variability of expression of the gene products in tissues of plants.

CaMV is a caulimovirus, a subgroup of pararetroviruses that has icosahedral capsids and infects only dicots, although the CaMV35 S promoter is a strong promoter in monocots. Sugarcane bacilliform virus (ScBV), Commelina yellow mottle virus (CoYMV) and rice tungro bacilliform virus (RTBV) are badnaviruses, a subgroup of pararetroviruses that have bacilliform capsids and infect mainly monocots. A promoter fragment isolated from CoYMV confers a tissue-specific pattern of expression that is different than the pattern conferred by the CaMV35S promoter. Transformed tobacco plants containing the CoYMV promoter linked to the beta-glucuronidase reporter gene ("GUS"; uidA) showed that while the CoMYV promoter is active in all organs, beta-glucuronidase activity occurs primarily in the phloem, the phloem-associated cells, and the axial parenchyma of roots, stems, leaves, and flowers (Medberry et al., *Plant Cell*, 4, 185 (1992); Medberry and Olszewski, *Plant J.*, 3, 619 (1993)). In contrast, the CaMV35S promoter is active in most cell types (Medberry et al., *Plant Cell*, 4, 185 (1992); Medberry and Olszewski, *Plant J.*, 3, 619 (1993)). Moreover, the CoYMV promoter is 30% as active in tobacco suspension cells and up to 25% as active in maize suspension cells compared to a duplicated CaMV35S promoter (Medberry et al., *Plant Cell*, 4, 185 (1992)).

Transgenic rice containing the RTBV promoter linked to the GUS gene showed strong phloem-specific promoter activity. This was consistent with the expression of this promoter in rice protoplasts. However, the RTBV promoter showed only weak activity in maize protoplasts (Bhattacharyya-Pakasi et al., *Plant J.*, 4, 71 (1993); Yin et al., *Plant J.*, 7, 969 (1995)). In contrast, the corresponding CaMV promoter shows strong promoter activity in protoplasts and in almost all tissues of transgenic plants (reviewed by Hohn and Fütterer, *Curr. Opin. Genet. Dev.*, 2, 90 (1992)).

Thus, what is needed is a highly expressed, constitutive promoter to express transgenes in fertile transgenic monocot and dicot plants.

SUMMARY OF THE INVENTION

The present invention provides an isolated and purified DNA molecule comprising a preselected DNA segment comprising a sugarcane bacilliform virus (ScBV) promoter, or a biologically active subunit thereof, that confers constitutively high levels of expression of operably linked preselected DNA segments in both monocot and dicot plants, plant tissue, plant parts or plant cells. While the nucleotide sequence of the genome of ScBV is known (Bouhida et al., *J. Gen. Virol.*, 74, 1 (1993)), the location of a promoter for genomic length viral RNA was not apparent, even after nucleotide sequence comparisons of the ScBV genome with promoter sequences of closely related viruses, such as CoYMV and RTBV. Surprisingly, the ScBV promoter is a strong and constituitive promoter in many cell types, unlike the strong tissue specific expression observed for CoMYV and RTBV promoters. A preferred embodiment of the invention is a preselected DNA segment comprising a ScBV promoter comprising SEQ ID NO:3, i.e., a preselected DNA segment that corresponds to nucleotide positions 5999–7420 of the ScBV genome. As described herein below, the ScBV promoter confers constitutive and vascular gene expression in *A. sativa* and *A. thaliana*. Thus, the ScBV promoter can be employed for constitutive or tissue-specific plant and non-plant gene expression in monocots and dicots. For example, the ScBV promoter may be linked to genes which confer to crops resistance against pests which attack crop grasses at the stem, e.g., aphids which vector barley yellow dwarf virus, or to confer tissue-specific resistance to dicotyledonous hosts, in which organs such as the roots are targeted by pathogens, e.g., soybean cyst nematode.

As used herein, "ScBV" includes any non-enveloped, bacilliform, DNA-containing badnavirus capable of systemically infecting Saccharum or related genera. Other distinguishing features of badnaviruses are described by Lockhart and Olszewski, in *The Encyclopedia of Virology*, Webster and Granoff (eds.), Academic Press, New York, N.Y. (1994)).

As used herein, the term "ScBV promoter" means a nucleotide sequence which, when that sequence is operably linked to a preselected DNA segment that encodes a protein, RNA transcript, or mixture thereof, results in the expression of the linked preselected DNA segment, i.e., the encoded RNA and/or protein. A preferred ScBV promoter has at least about 60%, preferably at least about 80%, more preferably at least about 90%, and even more preferably at least about 95%, nucleotide sequence identity to SEQ ID NO:3, SEQ ID NO:4 or SEQ ID NO:5. Another preferred embodiment of the invention is a ScBV promoter which comprises the minimum number of contiguous nucleotides which initiate RNA transcription.

As used herein, "biologically active" means that the promoter has at least about 0.1%, preferably at least about 10%, and more preferably at least about 25%, the activity of the ScBV promoter comprising SEQ ID NO:3, SEQ ID NO:4 or SEQ ID NO:5. The activity of a promoter can be determined by methods well known to the art. For example, see Medberry et al., *Plant Cell*, 4, 185 (1992); Medberry et al., The *Plant J.*, 3, 619 (1993); Sambrook et al., In: *Molecular Cloning: A Laboratory Manual* (1989); McPherson et al., U.S. Pat. No. 5,164,316.

Further provided is an expression cassette comprising a first preselected DNA segment comprising a ScBV promoter functional in a host cell, operably linked to a second preselected DNA segment encoding a protein, RNA transcript, or a combination thereof. A preferred host cell is a plant cell, e.g., a monocot or dicot cell. Another preferred embodiment of the invention is an expression cassette comprising a ScBV promoter operably linked to a selectable marker gene. Yet another preferred embodiment of the invention is an expression cassette comprising a ScBV promoter which comprises SEQ ID NO:3.

The invention also provides methods of selecting stable genetic transformants from transformed plant cells and methods of producing fertile transgenic plants from said transformed plant cells. The method for producing transformed plant cells comprises introducing into regenemble plant cells a recombinant DNA segment which comprises a first preselected DNA segment comprising a ScBV promoter operably linked to a second preselected DNA segment so as to yield transformed cells. Then a transformed cell line is identified or selected. Exemplary transformation methods include the use of microprojectile bombardment to introduce a preselected DNA segment, encoding a phenotypically observable or detectable trait, operably linked to the ScBV promoter, into regenerable monocot plant cells. A preferred embodiment of the invention is a method whereby the expression of the recombinant DNA segment in the transformed cells imparts a phenotypic characteristic to the transformed cells, such as herbicide or antibiotic resistance.

As used herein, the term "recombinant DNA segment" refers to a nucleic acid, i.e., to DNA, that has been derived or isolated from any appropriate tissue source and isolated from association with other components of the cell, such as nucleic acid or protein. The DNA may be subsequently chemically altered in vitro, so that its sequence is not naturally occurring, or corresponds to naturally occurring sequences that are not positioned as they would be positioned in a genome which has not been transformed with exogenous DNA, so that it can be sequenced, replicated, and/or expressed.

A preferred isolated recombinant DNA segment includes a first preselected DNA segment comprising a ScBV promoter functional in a plant cell operably linked to second preselected DNA segment comprising a selectable marker gene. Another preferred isolated recombinant DNA segment includes a second preselected DNA segment that corresponds to a gene that is already present in the plant genome, or one which is not normally present in the plant genome, which confers an agronomically useful phenotype to the plant, e.g., pest resistance. If the preselected DNA segment is normally present in the plant genome it may not be expressed or not highly expressed. Thus, the preselected DNA segment is introduced so as to alter the expression of the protein or RNA transcript encoded by the preselected DNA segment in the cells of the plant.

The invention also provides a method for producing a fertile transgenic plant. The method comprises introducing a recombinant DNA segment which comprises a first preselected DNA segment comprising a ScBV promoter operably linked to a second preselected DNA segment into regenerable plant cells so as to yield regenerable transformed cells. A population of transformed cells is selected or identified and a fertile transgenic plant is regenerated therefrom. The recombinant DNA segment is transmitted through a complete sexual cycle of said transgenic plant to its progeny so that it is expressed by the progeny plants. Thus, the invention also provides a transgenic plant, and seed, other plant parts, tissue, and progeny plants derived therefrom.

The transgenic plants of the invention include, but are not limited to, a transgenic T0 or R0 plant, i.e., the first plant regenerated from transformed plant cells, a transgenic T1 or R1 plant, i.e., the first generation progeny plant, and progeny plants of further generations derived therefrom which comprise and express the recombinant DNA segment. Microprojectile bombardment can be used to introduce the recombinant DNA segment into regenerable monocot cells, while Agrobacterium-mediated DNA transfer can be used to introduce the recombinant DNA into regenerable dicot cells.

Also provided is a transformed monocot or dicot plant, the cells of which comprise a recombinant DNA segment comprising a first preselected DNA segment comprising a sugarcane bacilliform virus promoter operably linked to a second preselected DNA segment The second preselected DNA segment is expressed in the transformed cells in an amount that is different than the amount in the cells of a plant in which cells only differ from the transformed cells in that the recombinant DNA segment is absent Such cells can include untransformed cells of the same part of the transformed, or transgenic, plant, in some cases. The second preselected DNA segment is expressed so as to render the transformed plant or a part thereof identifiable over the corresponding untransformed plant or part thereof.

The recombinant DNA segment is transmitted through a complete normal sexual cycle of the transformed plant to the next generation.

Also provided is a method comprising obtaining progeny from a fertile transgenic plant obtained by the method described hereinabove.

As used herein, the term "transgenic" or "transformed" with respect to a plant cell, plant part (including seed), plant tissue or plant means a plant cell, plant part, plant tissue or plant which comprises an isolated, purified preselected DNA segment which has been introduced into the genome of a plant cell, plant part, plant tissue or plant by a "genetic engineering" transformation method. That is, the genome of a transgenic plant cell, plant part, plant tissue or plant has been augmented by at least one preselected DNA segment. The term "wild type," "native," or "nontransgenic" refers to an untransformed plant cell, plant part, plant tissue or plant, i.e., one where the genome has not been altered by the presence of the preselected DNA segment.

The transformation of the plants in accordance with the invention may be carried out in essentially any of the various methods available to those skilled in the art of plant molecular biology. These include, but are not limited to, microprojectile bombardment, microinjection, electroporation of protoplasts or cells comprising partial cell walls, silicon carbide fiber-mediated DNA transfer and Agrobacterium-mediated DNA transfer. Plants useful in the practice of the invention include, but are not limited to, oat, wheat, soybean, corn, tobacco, rice, barley, potato, tomato, lettuce, oilseed rape, cotton, flax, sugar beet, sorghum, sunflower, alfalfa, millet and rye.

BRIEF DESCRIPTION OF THE FIGURES

FIG. 1 depicts the deduced amino acid sequence (SEQ ID NO:1) of sugarcane bacilliform virus.

FIGS. 2A–2B depict the nucleotide sequence (SEQ ID NO:2) of sugarcane bacilliform virus.

DETAILED DESCRIPTION OF THE INVENTION

Figure 3:
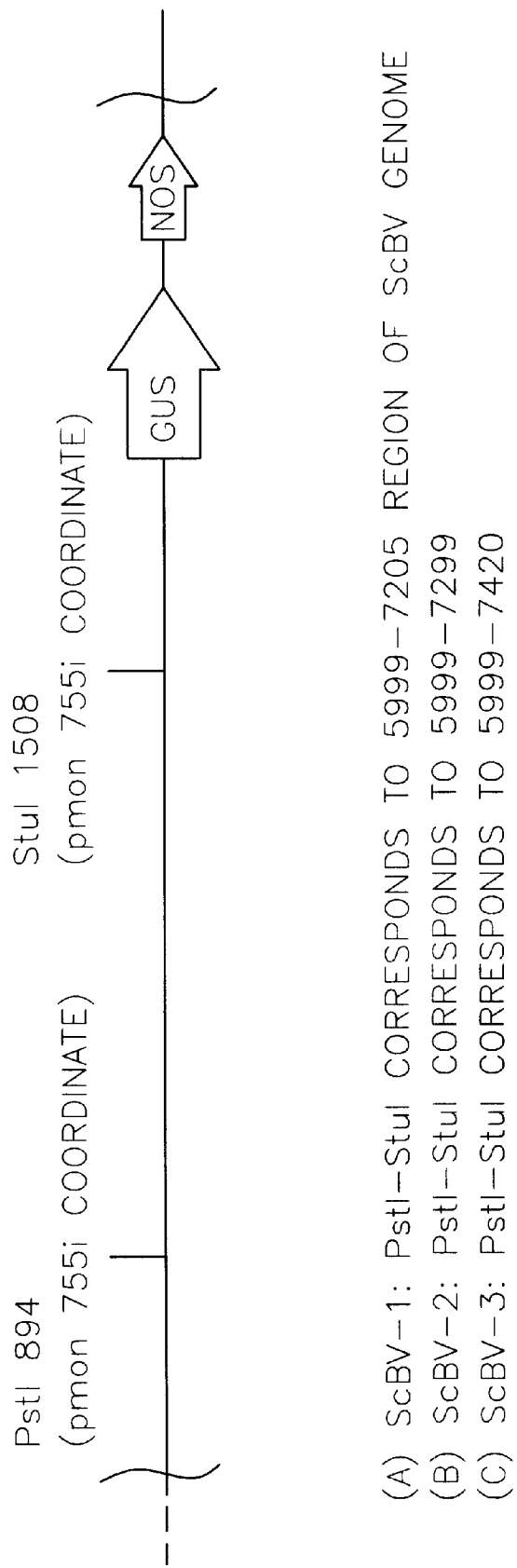
FIG. 3 depicts expression cassettes comprising an ScBV promoter useful for plant transformation.
Figure 4A:
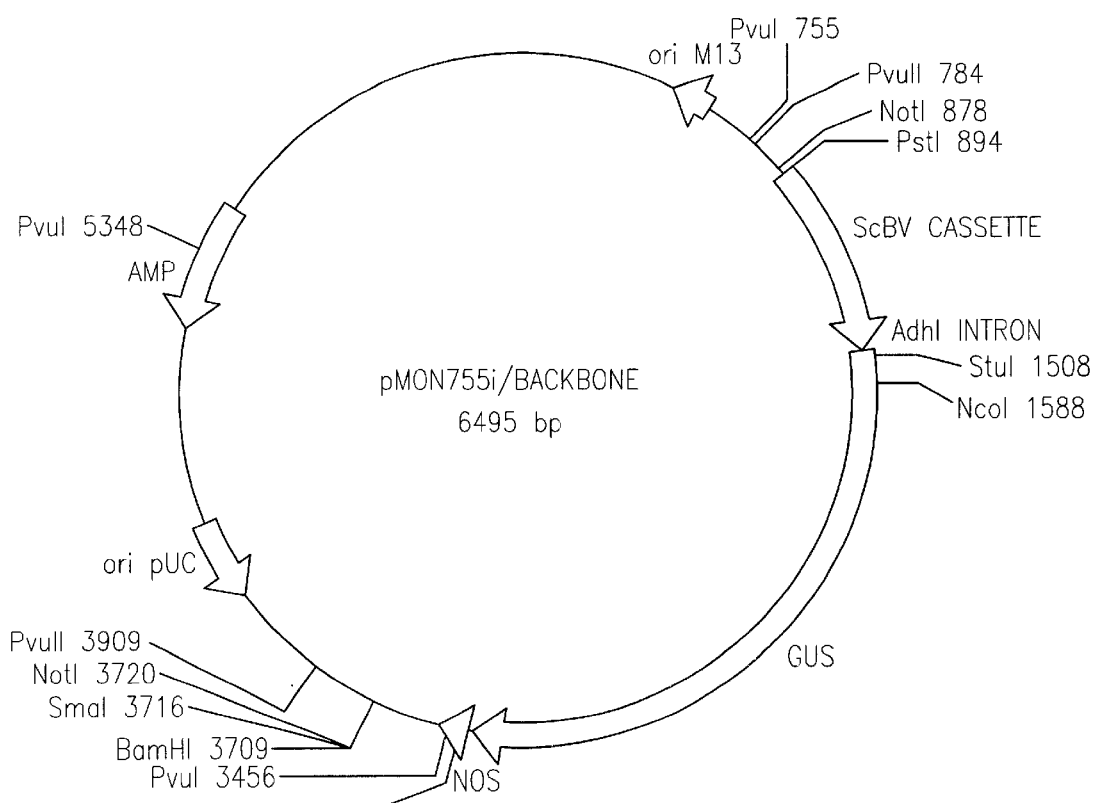
FIGS. 4A–4B depict a (A) map of constructs used to test ScBV promoter activity in *A. sativa*. Resulting pMON755i derivatives containing ScBV cassettes 1, 2, or 3 were designated pScBV-1, pScBV-2, or pScBV-3, respectively; and (B) map of the reporter gene region in the binary vector used to test the ScBV-3 cassette promoter activity in *A thaliana*. The ScBV-3 cassette was cloned into the SalI and XbaI sites of pOCA101. The cloning steps resulted in removal of the SpeI/StuI sites and the SalI/XhoI sites.
Figure 4B:
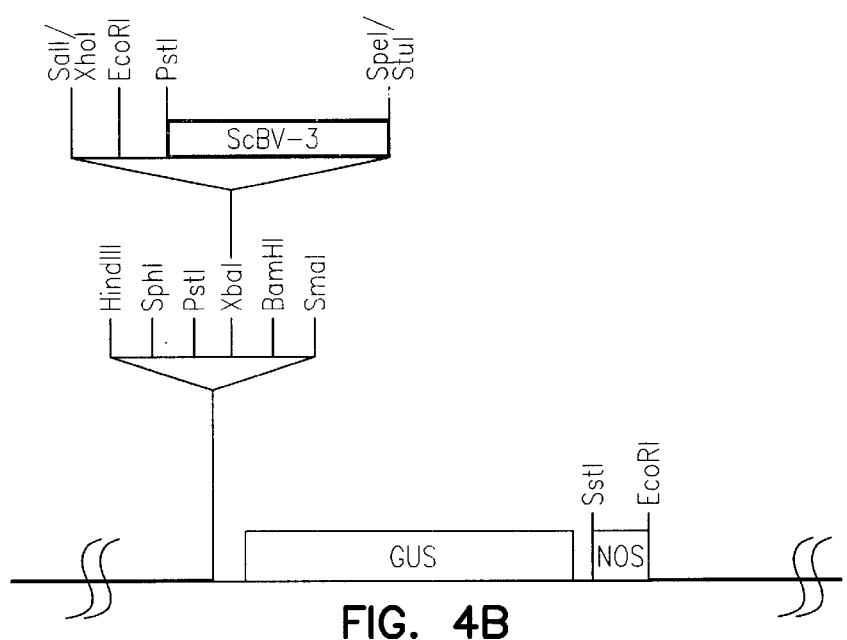

The introduction of exogenous genes (transgenes) into plants to provide a fertile transgenic plant with improved agronomic properties has the potential for long term improvement in, and expansion of, agriculture world-wide. The present invention provides constituitive and strong expression of transgenes, e.g., encoding substances that yield altered agronomic or physiologic traits, in plants. Such transgenic plants, and seeds derived therefrom, can sexually transmit this trait to their progeny. Exemplary traits for transgenic plants include increased stress tolerance, pest resistance, disease resistance (e.g., bacteria, viruses and fungi), improved yields, improved nutritional value, and improved grain composition or quality.

To provide constituitive and strong expression of transgenes in plants, plant cells, plant tissues, or plant parts, a sugarcane bacilliform virus promoter, e.g., comprising SEQ ID NO:3, is operably linked to a defined transgene, i.e., a preselected DNA segment, and introduced into regenerable plant cells. The resulting regenerated transgenic plant expresses the protein, or RNA transcript, encoded by the preselected DNA segment at a high and uniform level, preferably throughout the tissues and cells of the transformed plant. A preferred ScBV promoter sequence is located between nucleotides 5999 and 7420 (SEQ ID NO:3) of the ScBV genome(SEQ ID NO:2). A 5' non-translated leader sequence is preferably coupled with the promoter. The leader sequence can be from the ScBV genome itself or can be from a source other than ScBV, e.g., the maize alcohol dehydrogenase first intron, and the 5' non-translated leader sequences from petunia HSP 70 (Winter et al., *Mol. Gen. Genet.*, 211, 315 (1988); soybean HSP17.9 (Raschke et al., *J. Mol. Biol.*, 199 549(1988); or maize HSP70 (Rochester et al., *EMBO J.*, 5, 541 (1986)).

I. Recipient Cells

The present invention employs recipient plant cells that are susceptible to transformation and subsequent regeneration into stably transformed, fertile plants. For monocot transformation for example, immature embryos, meristematic tissue, gametic tissue, embryogenic suspension cultures or embryogenic callus tissue can be employed as a source of recipient cells which is useful in the practice of the invention. Preferred recipient cells for the transformation of oat are oat callus cultures initiated from immature embryos. To provide such a culture of recipient oat cells, immature embryos of oat are dehulled and sterilized. The embryos are incubated in liquid media overnight and then the embryos are excised and placed on solid media, scutellum side down to initiate a callus culture. A preferred solid media for initiating a callus culture is MS2D (see Torbert et al., *Plant Cell Reports*, 14, 635 (1995)).

For dicot transformation, organ and tissue cultures can be employed as a source of recipient cells. Thus, tissues, e.g., leaves, seed and roots, of dicots can provide a source of recipient cells useful in the practice of the invention.

Cultured susceptible recipient cells are preferably grown on solid supports. Nutrients are provided to the cultures in the form of media and the environmental conditions for the cultures are controlled. Media and environmental conditions which support the growth of regenerable plant cultures are well known to the art.

II. DNA Sequences

Virtually any DNA composition may be used for delivery to recipient plant cells to ultimately produce fertile transgenic plants in accordance with the present invention. The DNA segment or gene chosen for cellular introduction will often encode a protein and can be expressed in the resultant transformed cells, to result in a screenable or selectable trait and/or to impart an improved phenotype to the regenerated plant. The DNA segment or gene chosen for cellular introduction may also encode anti-sense RNA, i.e., a complement of a predetermined RNA molecule, or a portion thereof, that is expressed in an untransformed plant cell. The transcription of an anti-sense RNA suppresses the expression of the complementary RNA, e.g., one which encodes an undesirable property. Thus, a preselected DNA segment, in the form of vectors and plasmids, or linear DNA fragments, in some instances containing only the DNA element to be expressed in the plant, and the like, may be employed. However, this may not always be the case, and the present invention also encompasses transgenic plants incorporating non-expressed transgenes. Exemplary DNA sequences are provided in Tables 1, 2 and 3 in Weising et al. (*Ann. Rev. Genet.*, 22, 421 (1988)), and in Lundquist et al. (U.S. Pat. No. 5,484,956), both of which are incorporated by reference herein.

In certain embodiments, it is contemplated that one may wish to employ replication-competent viral vectors in plant transformation, such as those which can be employed for corn transformation, to transfer the preselected DNA segment into plants. Such vectors include, for example, wheat dwarf virus (WDV) "shuttle" vectors, such as pW1-11 and PW1-GUS (Ugaki et al., *Nucl. Acid Res.*, 19, 391 (1991)). These vectors are capable of autonomous replication in corn cells as well as *E. coli*, and as such may provide increased sensitivity for detecting DNA delivered to transgenic non-corn plant cells.

A replicating vector may also be useful for delivery of genes flanked by DNA sequences from transposable elements such as Ac, Ds, or Mu, as these elements would actively promote integration of the desired DNA and hence increase the frequency of stable transformation. It is also contemplated that transposable elements would be useful to introduce DNA fragments lacking elements necessary for selection and maintenance of the plasmid vector in bacteria, e.g., antibiotic resistance genes and origins of DNA replication.

DNA useful for introduction into plant cells includes that which has been derived or isolated from any source, that may be subsequently characterized as to structure, size and/or function, chemically altered, and later introduced into plants. An example of such DNA "isolated" from a source would be a useful DNA sequence that is excised or removed from said source by chemical means, e.g., by the use of restriction endonucleases, so that it can be further manipulated, e.g., separated or amplified, e.g., via polymerase chain reaction (PCR), for use in the invention, by the methodology of genetic engineering. Recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.*, 9, 6103 (1981), and Goeddel et al., *Nucleic Acids Res.*, 8, 4057 (1980). Thus, DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell.

An example of DNA "derived" from a source, would be a DNA sequence or segment that is identified as a useful fragment within a given organism, and which is then chemically synthesized in essentially pure form. Therefore, "recombinant or preselected DNA" includes completely synthetic DNA sequences, semi-synthetic DNA sequences, DNA sequences isolated from biological sources, and DNA sequences derived from RNA, as well as mixtures thereof.

The introduced DNA includes, but is not limited to, DNA from plant genes, and non-plant genes such as those from bacteria, yeasts, animals or viruses. Moreover, it is within the scope of the invention to isolate a preselected DNA segment from a given plant genotype, and to subsequently introduce multiple copies of the preselected DNA segment into the same genotype, e.g., to enhance production of a given gene product. The introduced DNA can include modified genes, portions of genes, or chimeric genes, including genes from the same or different plant genotype. The term "chimeric gene" or "chimeric DNA" is defined as a gene or DNA sequence or segment comprising at least two DNA sequences or segments from species which do not combine DNA under natural conditions, or which DNA sequences or segments are positioned or linked in a manner which does not normally occur in the native genome of the untransformed plant.

The introduced DNA used for transformation herein may be circular or linear, double-stranded or single-stranded. Generally, the DNA is in the form of chimeric DNA, such as plasmid DNA, that can also contain coding regions flanked by regulatory sequences which promote the expression of the recombinant DNA present in the resultant plant.

Generally, the introduced DNA will be relatively small, i.e., less than about 30 kb to minimize any susceptibility to physical, chemical, or enzymatic degradation which is known to increase as the size of the DNA increases. As noted above, the number of proteins, RNA transcripts or mixtures thereof, encoded by the DNA molecules which are introduced into the plant genome is preferably preselected and defined, e.g., from one to about 5–10 such products of the introduced DNAs may be formed.

A. Preparation of an Expression Cassette

An expression cassette of the invention can comprise a recombinant DNA molecule containing a preselected DNA segment operably linked to a ScBV promoter functional in a host cell, preferably a plant cell. Preferably, the expression cassette itself is chimeric, i.e., the cassette comprises DNA from at least two different species, or comprises DNA from the same species, which is linked or associated in a manner which does not occur in the "native" or wild type of the species.

1. DNA Molecules of the Invention Which Comprise a ScBV Promoter

A promoter is a region of DNA that regulates gene expression. Promoter regions are typically found in the flanking DNA sequence upstream from the coding sequence in viruses as well as prokaryotic and eukaryotic cells. A promoter sequence provides for regulation of transcription of the downstream gene sequence and typically includes from about 50 to about 2,000 nucleotide base pairs. Promoter sequences can also contain regulatory sequences such as enhancer sequences that can influence the level of gene expression. Some isolated promoter sequences can provide for gene expression of heterologous DNAs, that is a DNA different from the native or homologous DNA. Promoter sequences are also known to be strong or weak or inducible. A strong promoter provides for a high level of gene expression, whereas a weak promoter provides for a very low level of gene expression. An inducible promoter is a promoter that provides for turning on and off of gene expression in response to an exogenously added agent or to an environmental or developmental stimulus. Promoters can also provide for tissue specific or developmental regulation. An isolated promoter sequence that is a strong promoter for heterologous DNAs is advantageous because it provides for a sufficient level of gene expression to allow for easy detection and selection of transformed cells and provides for a high level of gene expression when desired.

The DNA molecule of the invention comprises a preselected DNA segment comprising a sugarcane bacilliform virus (ScBV) promoter. ScBV is a pararetrovirus. In general, pararetroviruses have a promoter that directs transcription of an RNA transcript that serves as both a template for replication of the viral genome and as mRNA. During replication of the circular double stranded viral DNA, the 3' end of a host tRNA binds near the 5' end of the ScBV transcript so as to prime DNA synthesis by the virally encoded reverse transcriptase. Thus, in general, ScBV promoters are positioned 5' to the tRNA binding site and 3' to the 5' half of the third open reading frame (ORF III) in the viral genome. Promoters from ScBV isolates can be prepared by purifying virions and/or viral DNA by methodology described in Bouhida et al. (supra), and the promoter region cloned using methods well known to the art, e.g., screening a DNA expression library generated by ligating ScBV viral DNA fragment with a screenable marker gene. In the alternative, a ScBV promoter can be amplified from viral DNA using a degenerate primer, e.g., BADNAT (Lockhart and Olszewski, In: Proceedings of INIBAP Conference on Breeding Banana and Plantains for Pest and Disease, pp. 105–113 (1994)) and a primer that hybridizes to a conserved region of the viral genome, e.g., the tRNA binding site or the DNA which encodes the viral replicase.

A preferred embodiment of the invention is an isolated and purified DNA molecule comprising a preselected DNA segment comprising a ScBV promoter comprising SEQ ID NO:3, SEQ ID NO:4 or SEQ ID NO:5, or a nucleotide sequence variant thereof (see below). It is also preferred that the ScBV promoter containing DNA excludes sequences that inhibit or interfere with translation of the RNA transcript generated by the ScBV promoter, e.g., the RNA transcript has a high degree of secondary structure or encodes potential start (ATG) codons.

A preselected DNA segment can be combined with the ScBV promoter by standard methods as described in Sambrook et al., In: *Molecular Cloning: A Laboratory Manual*, Cold Spring Harbor (1989)). Briefly, the preselected DNA segment can be subcloned downstream from the promoter using restriction enzymes to ensure that the DNA is inserted in proper orientation with respect to the promoter so that the DNA can be expressed. Once the preselected DNA segment is operably linked to the promoter, the expression cassette so formed can be subcloned into a plasmid or other vectors.

2. Variants of the DNA Molecules of the Invention

Nucleic acid molecules encoding nucleotide sequence variants of the ScBV promoter comprising SEQ ID NO:3, SEQ ID NO:4 or SEQ ID NO:5, and the like, can be prepared by a variety of methods known in the art. These methods include, but are not limited to, isolation from a natural source (in the case of naturally occurring nucleotide sequence variants, e.g., from other isolates of ScBV, isolated from infected plant material) or preparation by oligonucleotide-mediated (or site-directed) mutagenesis, PCR mutagenesis, and cassette mutagenesis of an earlier prepared variant or a non-variant version of the ScBV promoter.

Oligonucleotide-mediated mutagenesis is a preferred method for preparing nucleotide substitution variants of the ScBV promoter. This technique is well known in the art as described by Adelman et al., *DNA*, 2, 183 (1983). Briefly, ScBV promoter DNA is altered by hybridizing an oligonucleotide encoding the desired mutation to a DNA template, where the template is the single-stranded form of a plasmid or bacteriophage containing the unaltered or native DNA sequence of the ScBV promoter. After hybridization, a DNA polymerase is used to synthesize an entire second complementary strand of the template that will thus incorporate the oligonucleotide primer, and will code for the selected alteration in the ScBV promoter.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. U.S.A.*, 75, 5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.*, 153, 3 (1987). Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, N.Y. 1989).

Alternatively, single-stranded DNA template may be generated by denaturing double-stranded plasmid (or other) DNA using standard techniques.

For alteration of the native DNA sequence, the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the ScBV promoter, and the other strand (the original template) encodes the native, unaltered sequence of the ScBV promoter. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(aS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101.

Embodiments of the invention include an isolated and purified DNA molecule comprising a preselected DNA segment comprising a ScBV promoter comprising SEQ ID NO:3, or nucleotide sequence variants of SEQ ID NO:3 which do not reduce the biological activity of the promoter.

3. Preferred Preselected DNA Segments

A preferred embodiment of the invention provides a method for the introduction of a preselected DNA segment into fertile plants, which, when the preselected DNA segment is expressed from the ScBV promoter in the plant, confers a desirable agronomic property to the plant. Such DNA segments or "genes" are disclosed, for example in Lundquist et al. (U.S. Pat. No. 5,484,956), Lundquist et al. (U.S. Pat. No. 5,508,468), Dobres (international application PCT/US95/11231) and by K. Weising et al. (*Ann. Rev. Genet.*, 22, 421 (1988), see Tables 1, 2 and 3), all of which are incorporated by reference herein. However, the present invention is not limited in scope to preselected DNA segments which encode a desirable agronomic property, as many other preselected DNA segments which encode proteins or RNA transcripts that confer desirable characteristics to plants are within the scope of the invention.

Preferred agronomic properties encoded by the preselected DNA segment include, but are not limited to, insect resistance or tolerance, herbicide resistance or tolerance, disease resistance or tolerance (e.g., resistance to viruses or fungal pathogens), stress tolerance (increased salt tolerance), improved food content or increased yields. For example, genetic studies have shown that for a plant to resist infection by a particular plant pathogen, the plant must have a resistance (R) gene which interacts directly or indirectly with a single avirulence (avr) gene which is present in the genome of the pathogen. Thus, the introduction a preselected DNA segment comprising a R gene into a plant which lacks the R gene can confer resistance to that plant to a pathogen which expresses the corresponding avr gene.

Enhanced resistance to fungal infections may be obtained by introducing a preselected DNA segment which encodes a pathogenesis related (PR) protein into a plant. PR proteins are proteins which are synthesized by cereals in response to infection by some pathogenic fungi (Scott, *Australasian Plant Path.*, 23, 154 (1994)).

Enhanced resistance to viral infections may be obtained by introducing a preselected DNA segment encoding a viral coat protein into a plant. For example, Nelson et al. (*Bio/technol.*, 6, 403 (1988)) disclose that the expression of the tobacco mosaic virus (TMV) coat protein in a tomato plant confers tolerance to the plant to TMV and to tomato mosaic virus (ToMV), a virus related to TMV. Clark et al. (International application PCT/EP92/03001) disclose that expression of maize dwarf mosaic virus coat protein in corn resulted in plants which exhibited reduced disease symptoms when exposed to the virus.

Vaeck et al. (*Nature*, 328, 33 (1987)) disclose that the expression of *Bacillus thurigenesis* (Bt) endotoxin genes in tobacco rendered those plants more tolerant to insect infestation. Lundquist et al. (U.S. Pat. No. 5,484,956) disclose that expression of genes encoding Bt endotoxin can impart insect resistance to transgenic maize.

Moreover, it is envisioned that more than one preselected DNA segment can be introduced into a plant. For example, a plasmid which contains a selectable marker gene (see below) and a gene which confers resistance to a particular virus, e.g., barley yellow dwarf virus, can be introduced into regenerable plant cells.

4. Optional Sequences in the Expression Cassette

The expression cassette can also optionally contain other DNA sequences.

a. Marker Genes

In order to improve the ability to identify transformants, one may desire to employ a selectable or screenable marker gene as, or in addition to, the expressible preselected DNA segment. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., β-glucuronidase). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

Elements of the present disclosure are exemplified in detail through the use of particular marker genes, however in light of this disclosure, numerous other possible selectable and/or screenable marker genes will be apparent to those of skill in the art in addition to the one set forth hereinbelow. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed monocot.

1. Selectable Markers

Possible selectable markers for use in connection with the present invention include, but are not limited to, a neo gene (Potrykus et al., *Mol. Gen. Genet.*, 199, 183 (1985)) which codes for kanamycin resistance and can be selected for using kanamycin, G418, and the like; the npt II gene which encodes paromomycin resistance; the hyg gene which encodes hygromycin B resistance; a bar gene which codes for bialaphos resistance; a gene which encodes an altered EPSP synthase protein (Hinchee et al., *Biotech.*, 6, 915 (1988)) thus conferring glyphosate resistance; a nitrilase gene such as bxn from *Klebsiella ozaenae* which confers resistance to bromoxynil (Stalker et al., *Science*, 242, 419 (1988)); a mutant acetolactate synthase gene (ALS) which confers resistance to imidazolinone, sulfonylurea or other ALS-inhibiting chemicals (European Patent Application 154,204, 1985); a methotrexate-resistant DHFR gene (Thillet et al., *J. Biol. Chem.*, 263, 12500 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0,218, 571, 1987). See also Table 1 of Lundquist et al. (U.S. Pat. No. 5,484,956).

An illustrative embodiment of a selectable marker gene capable of being used to select transformants is the gene that encodes the enzyme phosphinothricin acetyltransferase, such as the bar gene (see Somers et al., supra (1992)). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.*, 205, 42 (1986); Twell et al., *Plant Physiol.*, 91, 1270 (1989)) causing rapid accumulation of ammonia and cell death.

2. Screenable Markers

Screenable markers that may be employed include, but are not limited to, a β-glucuronidase or uidA gene (GUS) which encodes an enzyme for which various chromogenic substrates are known; an R-locus gene, which encodes a product that regulates the production of anthocyanin pigments (red color) in plant tissues (Dellaporta et al., in *Chromosome Structure and Function*, pp. 263–282 (1988)); a β-lactamase gene (Sutcliffe, *PNAS USA*, 75, 3737 (1978)), which encodes an enzyme for which various chromogenic substrates are known (e.g., PADAC, a chromogenic cephalosporin); a xylE gene (Zukowsky et al., *PNAS USA*, 80, 1101 (1983)) which encodes a catechol dioxygenase that can convert chromogenic catechols; an α-amylase gene (Ikuta et al., *Biotech.*, 8, 241 (1990)); a tyrosinase gene (Katz et al., *J. Gen. Microbiol.*, 129, 2703 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science*, 234, 856 (1986)), which allows for bioluminescence detection; or even an aequorin gene (Prasher et al., *Biochem. Biophys. Res. Comm.*, 126 1259 (1985)), which may be employed in calcium-sensitive bioluminescence detection, or a green fluorescent protein gene (Niedz et al., *Plant Cell Reports*, 14, 403 (1995)).

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening.

b. Other Sequences

Transcription enhancers or duplications of enhancers can be used to increase expression from a particular promoter. Examples of such enhancers include, but are not limited to, elements from the CaMV 35S promoter and octopine synthase genes (Last et al., U.S. Pat. No. 5,290,924, issued Mar. 1, 1994). It is proposed that the use of an enhancer element, such as the ocs element, and particularly multiple copies of the element, will act to increase the level of transcription from adjacent promoters when applied in the context of plant transformation.

As the DNA sequence inserted between the transcription initiation site and the start of the coding sequence, i.e., the untranslated leader sequence, can influence gene expression, one can also employ a particular leader sequence. Preferred leader sequence include those which comprise sequences selected to direct optimum expression of the attached gene, i.e., to include a preferred consensus leader sequence which can increase or maintain mRNA stability and prevent inappropriate initiation of translation (Joshi, *Nucl. Acid Res.*, 15, 6643 (1987)). Such sequences are known to those of skill in the art. However, some leader sequences, e.g., the leader sequence of RTBV, have a high degree of secondary structure which is expected to decrease mRNA stability and/or decrease translation of the mRNA. Thus, leader sequences which do not have a high degree of secondary structure or which have a high degree of secondary structure where the secondary structure does not inhibit mRNA stability and/or decrease translation, or leader sequences that are derived from genes that are highly expressed in plants, will be most preferred.

Regulatory elements such as Adh intron 1 (Callis et al., *Genes Develop.*, 1, 1183 (1987)), sucrose synthase intron (Vasil et al., *Plant Physiol.*, 91, 5175 (1989)) or TMV omega element (Gallie et al., *The Plant Cell*, 1, 301 (1989)) can also be included where desired. Other such regulatory elements useful in the practice of the invention are known to those of skill in the art.

Additionally, expression cassettes can be constructed and employed to target the gene product of the preselected DNA segment to an intracellular compartment within plant cells or to direct a protein to the extracellular environment. This can generally be achieved by joining a DNA sequence encoding a transit or signal peptide sequence to the coding sequence of the preselected DNA segment. The resultant transit, or signal, peptide will transport the protein to a particular intracellular, or extracellular destination, respectively, and can then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of gene product.

The transit or signal peptide encoded by the preselected DNA segment can be directed to a particular organelle, such as the chloroplast rather than to the cytoplasm. Thus, the expression cassette can further comprise a chloroplast transit peptide encoding DNA sequence operably linked between a ScBV promoter and the preselected DNA segment (for a review of plastid targeting peptides, see Heijne et al., *Eur. J. Biochem.*, 180, 535 (1989); Keegstra et al., *Ann. Rev. Plant Physiol. Plant Mol. Biol.*, 40, 471 (1989)). This is exemplified by the use of the rbcS (RuBISCO) transit peptide which targets proteins specifically to plastids. For example, see Glassman et al., U.S. Pat. No. 5,258,300.

It may be useful to target DNA itself within a cell. For example, it may be useful to target an introduced preselected DNA to the nucleus as this may increase the frequency of transformation. Within the nucleus itself, it would be useful to target a gene in order to achieve site-specific integration. For example, it would be useful to have a gene introduced through transformation replace an existing gene in the cell.

When the expression cassette is to be introduced into a plant cell, the expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. Preferred 3' elements are derived from those from the nopaline synthase gene of *Agrobacterium tumefaciens* (Bevan et al., *Nucl. Acid Res.*, 11, 369 (1983)), the terminator for the T7 transcript from the octopine synthase gene of *Agrobacterium tumefaciens*, and the 3' end of the protease inhibitor I or II genes from potato or tomato, although other 3' elements known to those of skill in the art can also be employed. These 3' nontranslated regulatory sequences can be obtained as described in An, *Methods in Enzymology*, 153, 292 (1987) or are already present in plasmids available from commercial sources such as Clontech, Palo Alto, Calif. The 3' nontranslated regulatory sequences can be operably linked to the 3' terminus of the preselected DNA segment.

An expression cassette can also be introduced into an expression vector, such as a plasmid. Plasmid vectors include additional DNA sequences that provide for easy selection, amplification, and transformation of the expression cassette in prokaryotic and eukaryotic cells, e.g., pUC-derived vectors, pSK-derived vectors, pGEM-derived vectors, pSP-derived vectors, or pBS-derived vectors. Thus, additional DNA sequences include origins of replication to provide for autonomous replication of the vector, selectable marker genes, preferably encoding antibiotic or herbicide resistance, unique multiple cloning sites providing for multiple sites to insert DNA sequences or genes encoded in the expression cassette, and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838, issued Jul. 10, 1990) as exemplified by vector pGA582. This binary Ti plasmid vector has been previously characterized by An and is available from Dr. An (see *Methods in Enzymology*, 153 292 (1987)). This binary Ti vector can be replicated in prokaryotic bacteria such as *E. coli* and Agrobacterium. The Agrobacterium plasmid vectors can be used to transfer the expression cassette to plant cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform plant cells.

III. DNA Delivery

The expression cassette or vector is then introduced into a recipient cell to create a transformed cell. For the introduction of an expression cassette into plant cells, the frequency of occurrence of plant cells receiving DNA is believed to be low. Moreover, it is most likely that not all recipient cells receiving DNA segments or sequences will result in a transformed cell wherein the DNA is stably integrated into the plant genome and/or expressed. Some may show only initial and transient gene expression. However, certain cells from virtually any plant may be stably transformed, and these cells regenerated into transgenic plants.

A preselected DNA segment may be delivered into plant cells or tissues, or prokaryotic or eukaryotic non-plant cells, by currently available methods including, but not limited to, protoplast transformation, tungsten whiskers (Coffee et al., U.S. Pat. No. 5,302,523, issued Apr. 12, 1994), directly by microorganisms with infectious plasmids, infectious viruses, the use of liposomes, microinjection by mechanical or laser beam methods, by whole chromosomes or chromosome fragments, electroporation, silicon carbide fibers, and microprojectile bombardment. A preferred embodiment of the invention accomplishes the introduction of a preselected DNA segment into monocot cells by methods of transformation especially effective for monocots, which include, but is not limited to, microprojectile bombardment (see Lundquist et al., U.S. Pat. No. 5,538,877).

Introduction and expression of foreign genes in dicotyledonous (broad-leafed) plants such as tobacco, potato and alfalfa has been shown to be possible using the T-DNA of the tumor-inducing (Ti) plasmid of *Agrobacterium tumefaciens* (See, for example, Umbeck, U.S. Pat. No. 5,004,863, and international application PCT/US93/02480). Using recombinant DNA techniques and bacterial genetics, a wide variety of foreign DNAs can be inserted into T-DNA in Agrobacterium. Following infection by the bacterium containing the recombinant Ti plasmid, the foreign DNA is inserted into the host plant chromosomes, thus producing a genetically engineered cell and eventually a genetically engineered plant. A second approach is to introduce root-inducing (Ri) plasmids as the gene vectors.

Dicots are susceptible to transformation by Agrobacterium. Recently, rice and corn, which are monocots, have been shown to be susceptible to transformation by Agrobacterium as well. However, many other important monocot crop plants including wheat, barley, oats, sorghum, millet, and rye have not yet been successfully transformed by Agrobacterium. The Ti plasmid, however, may be manipulated in the future to act as a vector for these other monocot plants. Additionally, using the Ti plasmid as a model system, it may be possible to artificially construct transformation vectors for these plants. Ti-plasmids might also be introduced into monocot plants by artificial methods such as microinjection, or fusion between monocot protoplasts and bacterial spheroplasts containing the T-region, which can then be integrated into the plant nuclear DNA.

Other transformation methods for dicots include the leaf disc method of Horsch et al. (*Science*, 227, 1229 (1985)) and as adapted by Fry et al. (*Plant Cell Reports*, 6, 321 (1987)) for *Brassica napus*.

IV. Production and Characterization of Stable Transgenic Plants

After effecting delivery of a preselected DNA segment to recipient cells by any of the methods discussed above, the next steps of the invention generally involve identifying the transformed cells for further culturing and plant regeneration. As mentioned above, in order to improve the ability to identify transformants, one may employ a selectable or screenable marker gene as, or in addition to, the expressible preselected DNA segment. In this case, one would then generally assay the potentially transformed cell population by exposing the cells to a selective agent or agents, or one would screen the cells for the desired marker gene trait.

A. Selection

An exemplary embodiment of methods for identifying transformed cells involves exposing bombarded cultures to a selective agent, such as a metabolic inhibitor, an antibiotic, herbicide or the like as described hereinabove. Cells which have been transformed and have stably integrated a marker gene conferring resistance to the selective agent used, will grow and divide in culture. Sensitive cells will not be amenable to further culturing.

It is further contemplated that combinations of screenable and selectable markers will be useful for identification of transformed cells. In some cell or tissue types, a selection agent, such as the antibiotic kanamycin or G418, may either not provide enough selective killing to clearly identify transformed cells, or may cause substantial nonselective inhibition of transformants and nontransformants alike, thus causing the selection technique to fail. It is proposed that selection with a growth inhibiting compound, such as an antibiotic, at concentrations below those that cause 100% inhibition followed by screening of growing tissue for expression of a screenable marker gene, such as gus (beta-glucuronidase) or lux (luciferase), would allow one to recover transformants from cell or tissue types that are not amenable to selection alone. Therefore combinations of selection and screening can enable identification of transformants in a wider variety of cell and tissue types.

B. Regeneration and Seed Production

Cells that survive the exposure to the selective agent, or cells that have been scored positive in a screening assay, may be cultured in media that supports regeneration of plants. The transformed cells, identified by selection or screening and cultured in an appropriate medium that supports regeneration, will then be allowed to regenerate into mature plants. After the plants have reached the stage of shoot and root development, they may be transferred to a greenhouse for further growth and testing.

Mature plants are then obtained from cell lines that are identified as expressing the preselected DNA segment. If possible, the regenerated plants are self pollinated. In addition, pollen obtained from the regenerated plants is crossed to seed grown plants of agronomically important plant genotypes. In some cases, pollen from plants of these genotypes is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to other plant genotypes in order to introgress the preselected DNA segment into the genome of the other plants. This process is referred to as backcross conversion. When a sufficient number of crosses to the recurrent parent have been completed in order to produce a product of the backcross conversion process that is substantially isogenic with the recurrent parent except for the presence of the introduced preselected DNA segment, the plant is self-pollinated at least once in order to produce a homozygous backcross converted plant containing the preselected DNA segment. Progeny of these plants are true breeding.

Alternatively, seed from transformed plants regenerated from transformed tissue cultures is grown in the field and self-pollinated to generate true breeding plants. Progeny from these plants become true breeding lines.

Once the initial breeding lines are selected, test crosses are made and hybrid seed is produced. The testcross hybrids and breeding populations are planted in several different arrays in the field. One scheme of evaluation is to grow populations of hybrid plants containing the preselected DNA segment in many different locations and measure the performance of the plants at these different locations. Yield information as well as other measures of plant health, superiority and viability are made. The information regarding the performance of these hybrids along with that of the performance of non-transformed hybrids is compared.

Upon the identification of the superior performance of transgenic plants, the parent selections are advanced and an inbred line is produced through conventional breeding techniques. Hybrid plants having one or more parents containing the preselected DNA segment are tested in commercial testing and evaluation programs and performance documented. This testing includes the evaluation of performance trials carried out over a wide geographical area, as well as the use of dedicated trials to reveal performance advantage and hence value.

An additional advantage of the expression of the preselected DNA segment is the superior performance of the parental lines in the production of hybrids.

C. Characterization

To confirm the presence of the preselected DNA segment (s) or "transgene(s)" in the regenerating plants, a variety of assays may be performed. Such assays include, for example, "molecular biological" assays well known to those of skill in the art, such as Southern and Northern blotting and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

1. DNA Integration, RNA Expression and Inheritance

Genomic DNA may be isolated from callus cell lines or any plant parts to determine the presence of the preselected DNA segment through the use of techniques well known to those skilled in the art. Note that intact sequences may not always be present, presumably due to rearrangement or deletion of sequences in the cell.

The presence of DNA elements introduced through the methods of this invention may be determined by polymerase chain reaction (PCR). Using this technique discreet fragments of DNA are amplified and detected by gel electrophoresis. This type of analysis permits one to determine whether a preselected DNA segment is present in a stable transformant, but does not prove integration of the introduced preselected DNA segment into the host cell genome. In addition, it is not possible using PCR techniques to determine whether transformants have exogenous genes introduced into different sites in the genome, i.e., whether transformants are of independent origin. It is contemplated that using PCR techniques it would be possible to clone fragments of the host genomic DNA adjacent to an introduced preselected DNA segment.

Positive proof of DNA integration into the host genome and the independent identities of transformants may be determined using the technique of Southern hybridization. Using this technique, specific DNA sequences that were introduced into the host genome and flanking host DNA sequences can be identified. Hence the Southern hybridization pattern of a given transformant serves as an identifying characteristic of that transformant. In addition, it is possible through Southern hybridization to demonstrate the presence of introduced preselected DNA segments in high molecular weight DNA, i.e., confirm that the introduced preselected DNA segment has been integrated into the host cell genome. The technique of Southern hybridization provides information that is obtained using PCR, e.g., the presence of a preselected DNA segment, but also demonstrates stable integration into the genome and characterizes each individual transformant.

It is contemplated that using the techniques of dot or slot blot hybridization which are modifications of Southern hybridization techniques one can obtain the same information that is derived from PCR, e.g., the presence of a preselected DNA segment.

Both PCR and Southern hybridization techniques can be used to demonstrate transmission of a preselected DNA segment to progeny. In most instances the characteristic Southern hybridization pattern for a given transformant will segregate in progeny as one or more Mendelian genes (Spencer et al., *Plant Mol. Biol.*, 18, 201 (1992); Laursen et al., *Plant Mol. Biol.*, 24, 51 (1994)) indicating stable inheritance of the gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced preselected DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

2. Gene Expression

While Southern blotting and PCR may be used to detect the preselected DNA segment in question, they do not provide information as to whether the preselected DNA segment is being expressed. Expression may be evaluated by specifically identifying the protein products of the introduced preselected DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focussing, or by chromatographic techniques such as ion exchange or gel exclusion chromatography. Specific antibodies may be used to detect the unique structures of proteins via formats such as an ELISA assay, for example to detect npt II. Combinations of approaches may be employed to obtain even greater specificity such as western blotting, in which antibodies are used that bind to individual gene products that have been separated by electrophoretic techniques. Additional techniques may be employed to absolutely confirm the identity of the product of interest, such as evaluation by amino acid sequencing following purification. Although these procedures are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of preselected DNA segments encoding proteins which affect pigmentation of plant parts and may be detected phenotypically, or by a product, which is increased when the protein encoded by the preselected DNA segment is expressed, that may be analyzed by high performance liquid chromatography or ELISA (e.g., npt II).

D. Establishment of the Introduced DNA in Other Plant Varieties

Fertile, transgenic plants may then be used in a conventional plant breeding program in order to incorporate the preselected DNA segment into the desired lines or varieties.

Generally, the commercial value of the transformed plant produced herein will be greatest if the preselected DNA segment can be incorporated into many different hybrid combinations. A farmer typically grows several hybrids based on differences in maturity, standability, and other agronomic traits. Also, the farmer must select a hybrid based upon his or her geographic location since hybrids adapted to one region are generally not adapted to another because of differences in such traits as maturity, disease, drought and insect resistance. As such, it is necessary to incorporate the gene into a large number of parental lines so that many hybrid combinations can be produced containing the preselected DNA segment.

Plant breeding and the techniques and skills required to transfer genes from one line or variety to another are well known to those skilled in the art. Thus, introducing a preselected DNA segment, preferably in the form of recombinant DNA, into any other line or variety can be accomplished by these breeding procedures.

E. Uses of Transgenic Plants

The transgenic plants produced herein are expected to be useful for a variety of commercial and research purposes. Transgenic plants can be created for use in traditional agriculture to possess traits beneficial to the grower (e.g., agronomic traits such as resistance to water deficit, pest resistance, herbicide resistance or increased yield), beneficial to the consumer of the grain harvested from the plant (e.g., improved nutritive content in human food or animal feed), or beneficial to the food processor (e.g., improved processing traits). In such uses, the plants are generally grown for the use of their grain in human or animal foods. However, other parts of the plants, including stalks, husks, vegetative parts, and the like, may also have utility, including use as part of animal silage or for ornamental purposes. Often, chemical constituents of crops are extracted for foods or industrial use and transgenic plants may be created which have enhanced or modified levels of such components.

Transgenic plants may also find use in the commercial manufacture of proteins or other compounds, where the compound of interest is extracted or purified from plant parts, seeds, and the like. Cells or tissue from the plants may also be cultured, grown in vitro, or fermented to manufacture such molecules.

The transgenic plants may also be used in commercial breeding programs, or may be crossed or bred to plants of related crop species. Improvements encoded by the preselected DNA segment may be transferred, e.g., from cells of one plant species to cells of another plant species, e.g., by protoplast fusion.

The transgenic plants may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation. The methods of the invention may also be used to create plants having unique "signature sequences" or other marker sequences which can be used to identify proprietary lines or varieties.

The invention will be further described by the following examples.

EXAMPLE I

Expression Cassettes for Plant Transformation

To prepare an expression cassette comprising a ScBV promoter, three regions of the ScBV genome were amplified by polymerase chain reaction (PCR). The regions are upstream of open reading frames, upstream of a putative tRNA binding site, and do not include AUG codons. The PCR employed BamHI linearized pScBV-20 as the template (Bouhida et al., *J. Gen. Virol.*, 74, 1 (1993)). Primer pairs employed in the PCR are shown in Table 1. The amplification reactions resulted in the following regions of the ScBV genome being amplified: nucleotide positions 5999 to 7205 (amplified with primer ScBV-PRO FORW-5999, SEQ ID NO:6 and primer ScBV-PRO REV-7205, SEQ ID NO:7), 5999 to 7299 (amplified with primer ScBV-PRO FORW-5999, SEQ ID NO:6 and primer ScBV-PRO REV-7299, SEQ ID NO:8), and 5999 to 7420 (amplified with primer ScBV-PRO FORW-5999; SEQ ID NO:6 and primer ScBV-PRO REV-7420, SEQ ID NO:9) (according to the numbering system in Bouhida et al., supra). ScBV-PRO FORW-5999 was synthesized to include a PstI site. ScBV-PRO REV-7205, ScBV-PRO REV-7299 and ScBV-PRO REV-7420 were synthesized to include a StuI site. After amplification, the PCR products were digested with PstI and StuI and then gel purified.

To prepare monocot expression vectors, the gel fragments were ligated to pMON755i (Medberry and Olszewski, *Plant J.*, 3, 619 (1993)), which had been digested with PstI and StuI to remove the CaMV35S promoter fragment. pMON755i was derived from pMON755 (Medberry et al., *The Plant Cell*, 4, 185 (1992)) by inserting a modified maize alcohol dehydrogenase first intron segment 5' to the GUS gene. The resulting plasmids were designated ScBV-1 (5999-7205), ScBV-2 (5999-7299), and ScBV-3 (5999-7420).

TABLE 1

| Primer name | Sequence 5'-3' |
| --- | --- |
| SCBV-PRO FORW 5999 | CTCTAGCTGCAGGAAGTTGAAGACAAAAGAAG (SEQ ID NO: 6) |
| SCBV-PRO REV-7205 | GTACGTAGGCCTCACTGAATGGGCCCAGTAC (SEQ ID NO:7) |
| SCBV-PRO REV-7299 | TACGATAGGCCTTGGCAGACAAGGAATAAAG (SEQ ID NO:8) |
| SCBV-PRO REV-7420 | GCACGAAGGCCTTFGGTGAACTACCGATGATC (SEQ ID NO:9) |
| MAP-SCBV-GUS | CAGGACGGACCATGGATATATCTCC (SEQ ID NO:10) |

To prepare expression vectors for Agrobacterium-mediated transformation, a binary expression vector was constructed. ScBV-3 was digested with PstI and StuI and a 1.4 kb ScBV-containing fragment was ligated to pBluscript KS+ (Stratagene, La Jolla, Calif.), which had been digested with SpeI, the overhanging ends filled in with Klenow fragment, and then digested with PstI. From the resulting construct, a XhoI-XbaI fragment was isolated and ligated to pOCA101, which had been digested with SalI and XbaI. pOCA101 is a derivative of pOCA28 (Medberry et al., *Nucl. Acids Res.*, 18, 5505 (1990)) in which the polylinker is replaced by a HindIII-EcoRI fragment contaning the GUS gene. pOCA28 (Olszewski et al., *Nucl. Acids Res.*, 16, 10765 (1988)) has a $Sm^r/Spc^r$ gene from pHP45omega (Prenti and Kritsch, *Gene*, 28, 303 (1984)) which replaces a BglII/SmaI fragment containing a tetracycline resistance gene.

To map the transcription start site of a ScBV promoter, a labeled primer or DNA fragment and RNA generated from the ScBV promoter are employed in a primer extension reaction and/or a SI nuclease reaction. A primer useful to map the transcription start site of a ScBV promoter is shown in Table 1 (MAP-SCBV-GUS:SEQ ID NO:10).

EXAMPLE II

Monocot (Oat) Transformation with ScBV Promoter Constructs

Transient expression analyses in maize (using Black Mexican Sweet cells, "BMS" cells) and oat suspension cultures showed that ScBV-3 gave the highest levels of expression. In particular, in BMS cells, ScBV-3 conferred expression that gave rise to approximately 25 and 800 times more independent events that produced GUS expressing cells than the expression conferred by ScBV-2 or pScBV-1, respectively.

Immature embryos of oat (*Avena sativa L.* variety GP-1) were used to initiate callus. Friable embryogenic callus was visually selected using a low power microscope (6.6×) and subcultured every two weeks on MS2D medium containing MS salts (Torbert et al., supra). Callus derived tissue was plated onto solid MS2D medium containing 0.2 M sorbitol and 0.2 M mannitol as an osmoticum pretreatment for 4 hours prior to microprojectile bombardment as described by Vain et al. (*Plant Cell Reports*, 12, 84 (1993)).

In general, either tungsten (1.1 micron; M-17; Biorad Laboratories, Hercules, Calif.) or gold (1.0 micron; M-17; Biorad Laboratories, Hercules, Calif.) particles may be employed for microparticle bombardment. Approximately 60 mg of dry tungsten or gold particles is placed in 1 ml of 100% ethanol in a microtube. The tube is vortexed on high for 1–2 minutes, or sonicated using a standard tip at low power for 30 seconds. The vortexing is repeated three times. Then the microtube is subjected to centrifugation at 10,000 rpm for 1 minute. The supernatant is removed and 1 ml of sterile distilled water is added, the particles resuspended, centrifuged and the supernatant removed. This process is repeated once more. The particles are then resuspended in 1 ml sterile distilled water. Fifty microliters, enough for 4–8 bombardments, is aliquoted into microtubes while vortexing. Tungsten or gold aliquots are stored at −20° C.

To a single 50 microliter aliquot of particles under continuous agitation the following is added in the following order: 5 microliters of DNA (1 microgram/microliter), 50 microliters of 2.5 M $CaCl_2$ and 20 microliters of 0.1 M spermidine (free base, tissue culture grade, Sigma Chemical Co.). The mixture is vortexed for 3 minutes, subjected to centrifugation at 10,000 rpm for 10 seconds and the supernatant removed. The DNA coated particles are washed with 250 microliters of 100% ethanol by vortexing briefly, then subjected to centrifugation, and the supernatant removed. The particles are then resuspended in 60 microliters of 100% ethanol. 5–10 microliters of the suspension is then added to the center of the macrocarrier. The suspension is allowed to dry in a low-humidity and vibration-free environment for about 1 minute.

Approximately 800 mg of tissue was placed in the center of a Petri plate. The plate was positioned 5 cm below the stopping plate, and the tissue bombarded with gold particles coated with pScBV-3 and a plasmid that contains the nptII plant selectable marker linked to the CaMV35S promoter (pH24, see Torbert et al., supra) (0.625 micrograrns/bombardment), using Biolistic® PDS-1000/He Particle Delivery System (BioRad Laboratories, Hercules, Calif.) operated according to the manufacturer's instructions.

Tissue remained on the osmoticum medium (MS2D plus 0.4 M osmoticum) overnight and was transferred to MS2D maintenance media for 7 days at 20° C. in the dark. Transformed tissue was transferred to selection medium containing 50 mg/L paromomycin solidified with 0.35% low EEO Type I agarose (Sigma Chemical Co.) and subcultured every 2 weeks (Torbert et al., supra)). Growing colonies were isolated after about 6–8 weeks and allowed to grow for up to about 4 additional weeks. Shoots were regenerated in shoot regeneration medium (MS salts plus thiamine-HCl, 20 g/L sucrose, 2 mg/L NAA, 0.2 mg/L BAP, 50 mg/L paromomycin, pH 5.8, solidified with 0.35% low EEO Type I agarose). Roots were regenerated in root regeneration medium (MS salts plus thiamine-HCl solidified with 0.35% low EEO Type I agarose). Plants were then placed into soil and grown to maturity.

TABLE 2

| Tissue | Relative[1] Level of Expression[2] | # of Lines with Detectable Expression |
|---|---|---|
| Leaf* | + | 21•/23# (91.3%) |
| Stem | +++ | 21/23 (91.3%) |
| Peduncle | ++ | 20/23 (86.9%) |
| Rachis | ++ | 21/23 (91.3%) |
| Glume | ++ | 23/23 (100%) |
| Rachilla | ++ | 21/23 (91.3%) |
| Palea | +++ | 22/23 (95.6%) |
| Lemma | +++ | 22/23 (95.6%) |
| Anther | ++ | 20/23 (86.9%) |
| Ovary | +++ | 19/23 (82.6%) |
| Mature Seed | +++ | 2/2 (100%) |

[1]Relative level of detectable expression shown as (+) signs: (+), (++), and (+++) corresponds to low-medium, medium-high, and high-very high relative histochemical staining, respectively.
[2]Generalized expression pattern of the ScBV promoter based on 23 stably transformed, independent lines.
•Number of lines with detectable expression/#Number of lines examined.
*Vascular expression.

Figures 5A, 5B, 5C:
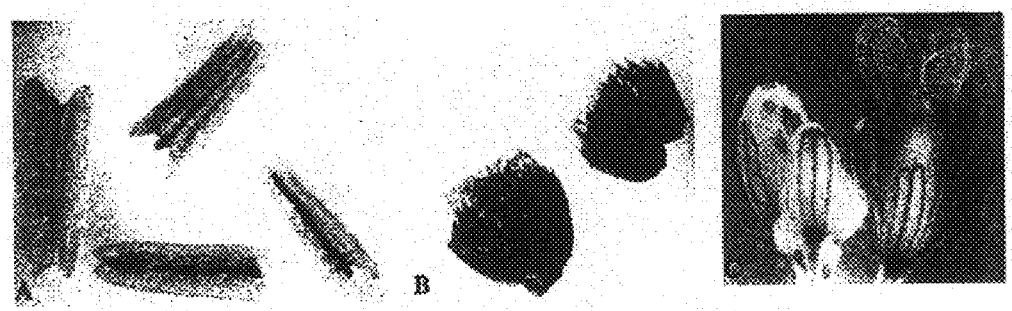
FIGS. 5A–5G depict *A. sativa* and *A. thaliana* tissues stained for GUS activity: (A) *A. sativa* anthers; (B) *A. sativa* ovaries; (C) *A. thaliana* floral organs; (D) *A. sativa* spiklet; (E) *A. sativa* stem; (F) *A. sativa* lead; (G) *A. thaliana* leaf.
Figures 5D, 5E, 5F, 5G:
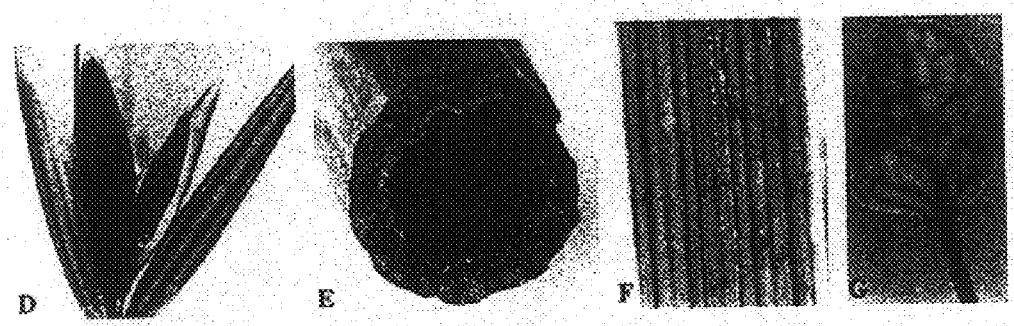

In stably transformed tissues of A. sativa, ScBV-3 conferred constitutive GUS expression in vegetative organs, most notably the stem (FIG. 5E). In the leaf, however, ScBV-3 conferred an expression pattern which is mostly, but not exclusively, confined to the vascular tissue (FIG. 5F). ScBV-3 also resulted in constitutive GUS expression in floral organs such as the palea, lemma, and the ovary (FIGS. 5D and 5B).

Regenerated plants (T0 generation) were screened for GUS activity. Fifty-six plants were recovered, and in some cases multiple plants were recovered from the same callus. Plants which were derived from the same callus were defined as one line. Since plants derived from the same callus could potentially represent independent events, data for plants recovered from an individual callus was pooled. Oat tissues were hand sectioned from plants with floral organs and green vegetative tissue.

Twenty three stably transformed independent lines were analyzed for GUS expression. Plant tissues were stained with GUS histochemical staining buffer in the presence of 1:5000 (v/v) dilution of the detergent Silwet L-77 (OSI Specialties, Charleston, W.Va.) and subjected to vacuum for 20 minutes. Tissues were stained for 8–48 hours at room temperature, destained for 24 hours and stored in 70% ethanol for analysis. GUS expression was scored under a dissecting microscope. The results of the GUS analysis are shown in Table 2. GUS activity was detected in almost all of the A. sativa organs tested, and lines with GUS activity in one organ tended to have activity in all of the organs tested. Stem, palea, lemma and ovary had the highest levels of expression. Moreover, of the twenty three independent lines tested, over 82% had detectable levels of GUS expression in leaf, stem, peduncle, rachis, glume, rachilla, palea, lemma, anther and ovary. Npt II levels in plant cells, parts or tissues are determined by an NPTII ELISA assay (5'→3', Boulder, Colo.) as also described in Torbert et al. (supra). Npt II is detected in all lines which express GUS.

A. sativa florets were collected from mature plants (no vegetative tissue). T1 seeds were produced by self-pollination of T0 plants. These seeds were dehulled and then sterilized by soaking first in 95% ethanol for 30 seconds, and then in 2.5% bleach and 1–2 drops of Tween-20/100 ml, for 5 minutes, followed by washing three times with sterile water. Seeds were germinated in magenta boxes on MS medium lacking hormones, grown for 10–12 days, and transferred to soil. Prior to transferring to soil, excised roots of the $T_1$ plants were subjected to staining for GUS gene expression as described above. A. sativa progeny ($T_1$) plants, and T1 seedlings, were subjected to analysis for GUS gene expression.

TABLE 3

GUS gene expression in A. sativa $T_1$ seedlings

| Tissue | Relative[1] level of expression[2] | No. Lines with Detectable expression |
|---|---|---|
| Leaf[&] | ++ | 8*/9#^ (88.9%) |
| Roots | ++ | 4/9 (44.4%) |
| Endosperm | + | 9/9 (100%) |

[1]The relative level of expression is indicated by the number of +'s: (+), (++), and (+++) corresponding to low-medium, medium-high, and high-very high histochemical staining, respectively.
[2]Generalized expression pattern of the ScBV-3 genomic region based on 9 stably-transformed, independent lines.
*Number of lines with detectable expression/#Number of lines examined.
[&]Vascular expression.
^Seedlings from nine lines were recovered in the $T_1$ generation.

Both seeds and T1 plants showed GUS activity, thus demonstrating that the GUS gene was heritable. The results of GUS analysis of T1 plants is shown in Table 4. Relative to the T0 plants, the level of expression in T1 appeared to be reduced in most organs (Table 2 and Table 4). This result suggests that the expression is reduced in the progeny.

TABLE 4

GUS gene expression in mature A. sativa $T_1$ plants

| Tissue | Relative[1] level of expression[2] | No. Lines with Detectable expression |
|---|---|---|
| Leaf[&] | + | 5*/7#^ (71.4%) |
| Stem | ++ | 5/7 (71.4%) |
| Peduncle | + | 3/7 (42.8%) |
| Rachis | + | 3/7 (42.8%) |
| Rachilla | + | 6/7 (85.7%) |
| Glume | ++ | 7/7 (100%) |
| Palea | ++ | 6/7 (85.7%) |
| Lemma | ++ | 6/7 (85.7%) |
| Anther | ++ | 3/7 (42.8%) |
| Ovary | ++ | 6/7 (85.7%) |
| Awn | − | 0/3 (0%) |

[1]The relative level of expression is indicated by the number of +'s: (+), (++), and (+++) corresponding to low-medium, medium-high, and high-very high histochemical staining, respectively.
[2]Generalized expression pattern of the ScBV-3 genomic region based on 7 stably-transformed, independent lines.
*Number of lines with detectable expression/#Number of lines examined.
[&]Vascular expression.
^Plants from seven out of the nine $T_1$ lines grew to maturity.

EXAMPLE III

Dicot (Arabidopsis) Transformation with ScBV Promoter Constructs

An expression vector which comprised a ScBV promoter linked to the GUS gene was transformed into *Arabidopsis thaliana* (Columbia ecotype) by vacuum infiltration essentially as described in van Hoof and Green, *Plant J.*, 10, 415 (1996); Bechtold et al., *C. r. Acad. Sci.*, 316, 1194 (1993) with the following modifications: 200 μl/L of Silwet L-33 was employed in the infiltration solution and *Agrobacterium*

*tumefaciens* strain C58C1 (MP 90) was employed as a non-eukaryotic host for the expression vector.

Seeds from plants which were subjected to the vacuum infiltration method (designated $T_1$ seeds) were sown on kanamycin-containing plates as described by Feldmann (In: "Methods in Arabidopsis Research" (C. Koncz, N.-H. Chua, and J. Schell, Eds.). World Scientific Publishing Co., Singapore. pp. 274–289 (1992)). Individual plants ($T_1$ plants) carrying the kanamycin marker gene were transferred to soil. Tissues from these plants were stained to localize GUS activity as described above for *A. sativa* tissue, except that the Silwet L-77 detergent was used at 1: 10,000 dilution (v/v) and the staining solution was vacuum infiltrated into the tissue by subjecting it to a vacuum for 5 minutes. Seeds of the $T_1$ plants ($T_2$ plants) were collected and progeny plants ($T_2$ plants) were also stained for GUS activity.

Tables 5 and 6 show the generalized pattern of expression of the ScBV promoter in T1 and T2 *A. thaliana* plants, respectively. Twenty-nine T1 plants were examined which were derived from 7 infiltrated plants. All transformed seedlings which were derived from a single infiltrated plant were grouped into one line.

In *A. thaliana* flowers, the expression pattern is mostly vascular, yet the stamen in some of the flowers exhibited constitutive GUS gene expression (FIG. 5C). When roots of *A. sativa* were stained, GUS expression was detected in 44% of the lines examined, whereas for *A. thaliana* roots, constitutive GUS gene expression was found in 86% of the lines examined.

TABLE 5

GUS gene expression in *A. thaliana* $T_1$ plants

| Tissue | Relative[1] level of expression[2] | No. Lines with Detectable expression |
| --- | --- | --- |
| Rosette Petiole | +++ | 4*/7# (57%) |
| Rosette leaf | ++ | 7/7 (100%) |
| Inflorescence stem | +++ | 3/7 (43%) |
| Peduncle | ++ | 4/7 (57%) |
| Flower sepal[&] | ++ | 4/7 (57%) |

[1]The relative level of expression is indicated by the number of +'s: (+), (++), and (+++) corresponding to low-medium, medium-high, and high-very high histochemical staining, respectively.
[2]Generalized expression pattern of the ScBV-3 genomic region based on 7 stably-transformed, independent lines.
*Number of lines with detectable expression/#Number of lines examined.
[&]Vascular expression.

TABLE 6

GUS gene expression in *A. thaliana* $T_1$ plants

| Tissue | Relative[1] level of expression[2] | No. Lines with Detectable expression |
| --- | --- | --- |
| Rosette Petiole | +++ | 7*/7# (100%) |
| Rosette leaf | +++ | 7/7 (100%) |
| Cauline Leaf | +++ | 7/7 (100%) |
| Inflorescence stem | ++ | 7/7 (100%) |
| Root | ++ | 6/7 (86%) |
| Flower sepal[&] | +++ | 7/7 (100%) |
| Silique[&] | +++ | 6/6 (100%) |
| Seed[@] | +++ | 4/6 (67%) |

[1]The relative level of expression is indicated by the number of +'s: (+), (++), and (+++) corresponding to low-medium, medium-high, and high-very high histochemical staining, respectively.
[2]Generalized expression pattern of the ScBV-3 genomic region based on 7 stably-transformed, independent lines.
*Number of lines with detectable expression/#Number of lines examined.

TABLE 6-continued

GUS gene expression in *A. thaliana* $T_1$ plants

| Tissue | Relative[1] level of expression[2] | No. Lines with Detectable expression |
| --- | --- | --- |

[&]Vascular expression.
[@]$T_3$ seeds.

EXAMPLE IV

Introduction of an ScBV Promoter Construct into Soybean Cells, Regeneration of Transformed R0 Plants and Progeny Production Soybean explants are derived from meristems excised from the embryonic axes of immature seeds. Prior to transformation, meristem explants are pre-incubated in high cytoknin-containing medium (Barwhale et al., *Planta*, 176, 473 (1986)) overnight. The bottom of a 60 mm Petri dish is filled with 1% water agar. The embryos are surface sterilized and plated unto the agar in the Petri dish.

A quantity of 1–3 micrometer gold beads (Alfa Chemical Co.) are precoated with polylysine by being rinsed in 0.02% polylysine and air drying. A linearized expression vector, which comprises a ScBV promoter sequence, e.g., linearized expression vector, which comprises a ScBV promoter sequence, e.g., SEQ ID NO:3, operably linked to a preselected DNA segment, is prepared. Preferably, the expression vector further comprises a marker gene, such as the neo gene (APT 3'II). 225 micrograms of the expression vector in aqueous solution is added to 35 mg coated gold beads and then sequentially 22 microliters of 10 mM $Na_2HPO_4$ and 22 microliters of 10 mM $CaCl_2$ which form a fine precipitate as the solution is dried under $N_2$. In general, 1.0 to 0.001 mg of DNA per mg of gold beads is prepared. The dried precipitate coated beads are then resuspended in 100% ethanol and deposited unto 2.0 millimeter plastic coated aluminized mylar sheets approximately 9 mm by 11 mm. The coated beads are applied to give a final density of 0.2 $mg/cm^2$ on the mylar carrier sheet. In general, the carrier sheet is loaded with 0.05–40 mg of loaded beads per square centimeter.

A vacuum of 500 mm of mercury is applied. A 24 kV discharge from the 2 microfarad capacitor is discharged through the electrodes accelerating the particles at the soybean embryo. The bombarded embryos are removed from the target surface and plated unto plates for organogenesis procedures. For example, see Barwhale et al., *Planta*, 176, 473 (1986)).

The explants are plated in the dark on MS basal medium as modified by Barwhale et al. (supra). Following incubation of 1 to 2 weeks in the dark, the tissues are transferred to the same basal medium which contains a lower level of cytokinin (1.7 micromolar), to promote shoot elongation. Shoots are harvested at 0.5 to 1.0 cm in height. Three to eight shoots are recovered per explant at 2–4 months.

After shoots reach 0.5–1.0 cm in height, they are grafted onto the roots of germinating approximately ten days old soybean seedlings. Prior to grafting they are hardened on ½ MS medium for one week. As soon as sufficient plant tissue is achieved, the tissues are assayed for the presence of the marker gene. For example, if the neo gene is used as a marker gene, APH 3'II activity is assayed in plant tissues.

The presence of the preselected DNA molecule of interest, e.g., encoding a viral coat protein, is detected by Southern blot analysis. Ten micrograms of genomic DNA from plant tissue is digested with an appropriate restriction enzyme. The DNA is then phenol:chloroform extracted and precipitated with ammonium acetate and ethanol. The digested DNA is fractionated on an agarose gel by electrophoresis. A $^{32}$P labeled probe corresponding to at least a portion of the DNA molecule of interest is employed. After washing the filter, the hybridizing DNA fragments are visualized by autoradiography. Plants are thus shown to carry the DNA molecule of interest.

A plant, the tissues of which demonstrate marker gene enzymatic activity or which are positive by Southern blot analysis for a DNA molecule of interest or the marker gene, is grown to maturity. The plant is self-pollinated and seeds recovered. Seedlings are employed to generate plants, the leaves of which are assayed for marker gene-associated enzymatic activity or by Southern blot analysis for the DNA molecule of interest.

EXAMPLE V

Introduction of a ScBV Promoter Construct into Tobacco Cells, Regeneration of Transformed R0 Plants and Progeny Production Tobacco (*Nicotiani tabacum var. samsun*) leaf disks with diameters of about 6 mm are taken from surface sterilized tobacco leaves. These are cultivated on MS104 agar medium for two days to promote partial cell wall formation at the wound surfaces. They are then submerged in a culture of *A. tumefaciens* cells containing a plasmid that has a ScBV promoter operably linked to a preselected DNA segment, e.g., encoding GUS, and another expression cassette encoding kanamycin resistance and pMP90RK, a helper plasmid, which is grown overnight in Luria broth at 28° C., and shaken gently. The cells are removed from the bacterial suspension, blotted dry, and incubated upside down on filter paper placed over "nurse" cultures of tobacco cells as described by Horsch (*In Vitro*, 16, 103 (1980)). After two or three days, the disks are transferred to petri dishes containing MS media with 500 μg/ml carbenicillin with no nurse culture.

Control tissue is created using *A. tumefaciens* cells containing the helper plasmid pMP90RK and a different plant transformation vector, pMON505, which contained a T-DNA region with a NOS/NPTII/NOS kanamycin resistance gene and a selectable marker gene.

Within ten days after transfer to the MS media, actively growing callus tissue appears on the periphery of all disks on both the control and transformed plates. Transformed tobacco plants are then produced by regeneration from the above-described transformed leaf disks by the procedure described by Horsch et al. (*Science*, 227, 1229 (1985)). The transformed plants obtained contain the expression cassette which contains the ScBV promoter fused to the β-glucuronidase gene.

The same procedure is used to obtain transformed tobacco with a CaMV35S promoter fused to the same preselected DNA segment, i.e., GUS.

Transformed plants containing the GUS gene driven by either the ScBV promoter or the CaMV35S promoter are assayed using a histological staining procedure to determine GUS activity in the transformed cells. The results of these assays on plants transformed with ScBV/GUS/NOS are compared to the results of the same assays performed on plants transformed with CaMV35S/GUS/NOS.

The histochemical assay of the tobacco plants containing the ScBV/GUS/NOS and CaMV35S/GUS/NOS constructs involves examination of plant organs and/or tissue sections of the transformed plants to determine GUS activity. The tissue or organ sections of the transformed plant are prepared by using a razor blade to free-hand section the plant tissue into sections less than 0.5 mm in thickness. The sections are then placed in excess X-gluc solution so that the section was fully covered. Pulling a vacuum on the sections can aid in penetration of X-gluc solution. A 50 ml X-gluc solution is prepared by combining 25 ml of 0.2 M Na$_3$PO$_4$ buffer pH 7.9, 24.0 ml dH$_2$O, 0.25 ml 0.1 M K$_3$[Fe(CN)$_6$], 0.25 ml 0.1 M K[Fe(CN)$_6$] and 0.5 ml 1 M EDTA, pH 7.0. To this solution, 50 mg of X-gluc (5-bromo-4-chloro-3-idilyl-β-glucuronide) obtained from Research Organics (Cleveland, Ohio) is added and stirred until dissolved. The solution is then preferably sterilized by filtration. The sections in the X-gluc solution are then placed at 37° C. for 2–4 hours. Care is taken to prevent evaporation of the solution. After the incubation period, the sections are rinsed with phosphate buffer, or distilled H$_2$O, and the sections were examined immediately with a dissecting scope or compound microscope. If there is interference from the pigments, the tissue can be fixed in FAA solution (85 ml 50% ethanol, 5 ml glacial acetic acid and 10 ml formalin) for 24 hours. Problems with phenolics can be mitigated by the addition of sodium metabisulfite to 20 mM to the staining solution just prior to staining. A positive test for the presence of GUS activity is shown by a blue coloration appearing in the tissue of the assayed plant section.

A histological staining assay is performed on a sections transformed with the β-glucuronidase gene driven by either the CaMV35S promoter or the ScBV promoter. A typical staining profile was observed for the CaMV35S promoter driven GUS gene with staining in some tissues and no staining in other tissues within a single transgenic plant. However, tissue from a plant transformed with the ScBV promoter driven GUS gene shows that the transformed plant exhibits a fair, preferably a much higher, level of GUS expression and a more uniform pattern of expression throughout the tissue and cells than observed in tissues from plants transformed with CaMV35S/GUS. This is illustrated by the predominant blue coloration throughout the section.

The distribution of expression and the number of highly expressing transgenic plants obtained show that the ScBV promoter is superior in tissue distribution and uniformity of expression when compared to the CaMV/GUS plants. Greater than 90% of the ScBV/GUS containing transformed plants show fair, preferably very strong GUS expression and that the staining is uniform from plant to plant and tissue to tissue. This staining is consistently as good in the ScBV containing plants as that in the CaMV/GUS plants.

In order to provide further evidence that the ScBV promoter is a strong and constitutively expressed promoter, transgenic *Nicotiana tabacum* plants containing the constructs are assayed for GUS activity using the fluorimetric assay of Jefferson et al. (*EMBO J.*, 6, 3901 (1987)) in extracted leaves, flowers stems and roots. Incubations are performed at 37° C. for 15 minutes. A 1 g 4th internode leaf, a flower, a 4 cm long stem section, or roots are excised. Selected tissue is extracted by freezing in liquid nitrogen, grinding with a mortar and pestle, and resuspending in 1 ml 0.1 M K$_3$PO$_4$ pH 7.8, mM EDTA, 10 mM DT, 0.8 mM PMSF, and 5% glycerol. The fluorogenic reaction was carried out in 2 mM 4-methyl umbelliferyl glucuronide. Fluorescence is measured using a Hoechst DNA fluorometer (Model TKO 100). Protein concentrations of plant extracts are determined by Bradford assay.

The CaMV35S promoter is arbitrarily given an expression level of "1" for each tissue analyzed and the relative expression level of the ScBV promoter is then determined. The GUS expression obtained with the ScBV promoter is found to be superior to that obtained with the CaMV35S promoter.

The invention is not limited to the exact details shown and described, for it should be understood that many variations and modifications may be made while remaining within the spirit and scope of the invention defined by the claims.

What is claimed is:

1. An isolated and purified DNA molecule comprising a promoter comprising SEQ ID NO:5, or a fragment thereof having promoter activity, wherein the DNA molecule does not encode a sugarcane bacilliform virus polypeptide.

2. The DNA molecule of claim 1 wherein the promoter consists of SEQ ID NO:3.

3. The DNA molecule of claim 1 wherein the promoter consists of SEQ ID NO:4.

4. The DNA molecule of claim 1 wherein the promoter consists of SEQ ID NO:5.

5. An expression cassette comprising a first DNA segment which comprises a promoter comprising SEQ ID NO:5, or a fragment thereof having promoter activity, functional in a plant cell operably linked to a second DNA segment encoding a protein or a RNA transcript, wherein the second DNA segment does not encode a sugarcane bacilliform virus polypeptide.

6. The expression cassette of claim 5 further comprising a third DNA segment encoding an amino terminal chloroplast transit peptide which is operably linked to the second DNA segment.

7. The expression cassette of claim 5 wherein the promoter consists of SEQ ID NO:3.

8. The expression cassette of claim 5 wherein the promoter consists of SEQ ID NO:4.

9. The expression cassette of claim 5 wherein the promoter consists of SEQ ID NO:5.

10. The expression cassette of claim 5 which further comprises an enhancer element.

11. The expression cassette of claim 5 wherein the second DNA segment encodes a selectable marker or a reporter protein.

12. The expression cassette of claim 5 wherein the promoter is constitutively expressed in the host cell.

13. The expression cassette of claim 5 wherein the plant cell is a dicot cell.

14. The expression cassette of claim 5 wherein the plant cell is a monocot cell.

* * * * *

UNITED STATES PATENT AND TRADEMARK OFFICE
CERTIFICATE OF CORRECTION

PATENT NO.   : 6,489,462 B1
DATED        : December 3, 2002
INVENTOR(S)  : Olszewski et al.

It is certified that error appears in the above-identified patent and that said Letters Patent is hereby corrected as shown below:

<u>Title page, Item [60] and Column 1, line 7,</u>
Delete "PCT/IB97/01338" and insert -- PCT/IB97/0338 --, therefor.

<u>Title page,</u>
Item [56], OTHER PUBLICATIONS", delete "Sugarcane Bacillifrom" and insert
-- Sugarcane Bacilliform --, therefor; and delete "The Plant Journal" and insert -- The Plant Journal --, therefor.

Signed and Sealed this

Ninth Day of September, 2003

JAMES E. ROGAN
*Director of the United States Patent and Trademark Office*

SEQUENCE LISTING

```
<160> NUMBER OF SEQ ID NOS:  10

<210> SEQ ID NO 1
<211> LENGTH: 1871
<212> TYPE: PRT
<213> ORGANISM: Sugarcane bacilliform virus

<400> SEQUENCE: 1

Met Thr Gln Arg Val Arg Gly Thr Gly Ser Ser Thr Ile Thr Glu Asp
  1               5                  10                  15

Gly Ala Leu Leu Asp His Gln Ile Arg Asp Tyr Arg Arg Ala Gln His
                 20                  25                  30

Ala Lys His Glu Ala Gln Arg Ile Ala Gly Gln Ala Leu Ala Phe Leu
             35                  40                  45

Arg Val Thr Ser Asp Asp Pro Arg Glu Lys Thr Leu Glu Met Leu Met
         50                  55                  60

Gln Pro Asp Val Glu Leu Thr Arg Ser Met Lys Lys Arg Ala Arg Ala
 65                  70                  75                  80

Phe Pro Ala Glu Val Leu Tyr Gly Pro Arg Ser Asp Asp Ile His His
                 85                  90                  95

Lys Val Phe Gln Gly Ser Ser Ser Gln Asp Ile Leu Leu Ile Asp Asp
                100                 105                 110

Asn Gln Leu Asp Met Thr Phe Ile Lys Glu Glu Thr Phe Glu Gln Leu
            115                 120                 125

Glu Gln Ala Gly Leu Arg Tyr Ile His Pro Gly Ile Leu Ala Val Arg
        130                 135                 140

Ile Gln Pro Leu His Pro Asp Trp Ser Gly Lys Leu Val Phe Ile Val
145                 150                 155                 160

Phe Arg Asp Ile Arg Asp Asn Pro Pro Arg Val Leu Gly Ala Met Glu
                165                 170                 175

Ile Asp Leu Ser Lys Gly Pro Gln Met Val Tyr Val Ile Asn Ser Phe
            180                 185                 190

Met Thr Thr Ile Lys Asp Phe Phe His Gly Ile Gln Leu Thr Val Lys
        195                 200                 205

Val Lys Gly Tyr Glu Gly Trp Gln Gly Glu Ala Asn Leu His Ile Glu
    210                 215                 220

Arg Leu Ile Thr Ala Arg Leu Ser Asn Thr Thr Asn Val Tyr Phe Lys
225                 230                 235                 240

Tyr Lys Val Glu Gly Val Ala Ser Phe Ile Lys Thr Lys Gly Ile Lys
                245                 250                 255

Ala Ile Glu Ala Thr Lys Lys Ser Val Lys Gly Ile Arg Gly Gly Glu
            260                 265                 270

Trp Asn Ile Leu Pro Ser Lys Leu Glu Val Val Met Gln Pro Thr Lys
        275                 280                 285

Val Gln Thr Thr Glu Asn Tyr Asp Gly Thr Thr Ser Phe Arg Phe Thr
    290                 295                 300

Asn Tyr Glu Gly Ala Ser Ser Ser Lys Pro Val Glu His Asn Ser Asp
305                 310                 315                 320

Asp Glu Ala Tyr Met Ala Leu Phe Glu Glu Glu Glu Glu Glu Asp Asp
```

-continued

```
                     325                 330                 335
Ile Thr Phe Leu Asn Arg Ile Leu Ser Lys Tyr Ser Thr Gln Gln Lys
                 340                 345                 350

Val Val Gly Glu Glu Phe Ser Pro Glu Asp Gln Ile Ile Ser
                 355                 360                 365

Asp Phe Leu Gly Lys Thr Glu Ala Tyr Pro Ala Glu Ile Glu Glu
    370                 375                 380

Glu Tyr Pro Ala Leu Arg Arg Leu Glu Gln Leu Met Lys Thr Lys Val
385                 390                 395                 400

Val Val Gln Glu Ile Glu Glu Pro Ser Gln Pro Val Glu Ala Lys Met
                405                 410                 415

Ser Thr Ser Thr Gly Ser Ser Ala Met Ile Pro Ala Asn Met Asp Met
                420                 425                 430

Asp Gly Asn Met Pro Gly Tyr Ala Pro Ala Gln Glu Ala Arg Gly Trp
            435                 440                 445

Asp Ser Gly Glu Thr Ser Arg Arg Asn Tyr Gly Gly His Ser Arg Lys
    450                 455                 460

Trp Lys Asp Glu Ser Gln Phe Phe Asn Leu Pro Ser Ala Met Ala Thr
465                 470                 475                 480

Ser Gly Ala Met Leu Val Leu Thr Met Gly Asn Tyr Ala Lys Glu Phe
                485                 490                 495

Asp Arg Trp Gln Ser Ile Asn Thr Asn Leu Leu Ala Ser Gln Thr Phe
            500                 505                 510

Glu Asn Ala Glu Asp Lys Ile Thr Arg Ile Glu Asn Leu Leu Gly Glu
        515                 520                 525

Thr Glu Lys Leu Met Phe Gln Thr Trp Arg Met Ala Phe Pro Thr Ala
    530                 535                 540

Phe Glu Ala Met Lys Thr Gln Ala Thr Gly Thr Asn Gly Thr Gln Asn
545                 550                 555                 560

Val Phe Ser Gln Met Lys Arg Ile Leu Leu Gly Glu Val Pro Glu Gln
                565                 570                 575

Gly Thr Thr Asn Thr Gln Asp Ala Ala Tyr Lys Arg Ile Lys Ser Leu
            580                 585                 590

Val Cys Gln Glu Met Thr Tyr Pro Ala Ile Met Arg Tyr Leu Val Gly
    595                 600                 605

Tyr Arg Asn Leu Ala Ala Arg Ser Gly Arg Ala Trp Val Asn Asn Glu
610                 615                 620

Leu Thr Asp Glu Phe Phe Thr Lys Leu Pro Gly Lys Leu Gly Asp Arg
625                 630                 635                 640

Val Lys Glu Ala Phe Lys Lys Tyr Pro Gly Val Glu Arg His Val
                645                 650                 655

Pro Ala Ala Thr Arg Phe Thr Tyr Asp Tyr Leu Glu Glu Ile Cys Thr
            660                 665                 670

Glu Asn Asn Phe Gln Lys Gln Leu Arg Ser Leu Asn Phe Cys Lys Gly
        675                 680                 685

Phe Pro Val Val Asn Pro Val Gly Thr Arg Lys Tyr Gly Lys Lys Tyr
    690                 695                 700

Gly Thr Arg Lys Ala Arg Ser Tyr Arg Gly Lys Pro His Lys Ser His
705                 710                 715                 720

Val Arg Ile Glu Lys Lys Lys Tyr Leu Gln Gln Arg Glu Lys Lys Cys
                725                 730                 735

Arg Cys Tyr Val Cys Gly Ser Pro Asp His Leu Met Lys Asp Cys Lys
                740                 745                 750
```

-continued

```
Ser Pro Met Lys Arg Gln Glu Arg Val Asn Leu Ala Asn Glu Leu Asp
        755                 760                 765
Ile Pro Asp Gly Tyr Asp Leu Val Ser Val Gly Tyr Asp Glu Ser Asp
    770                 775                 780
Ile Asp Glu Ile Tyr Ser Val Ser Glu Asn Glu Glu Cys Gln Ala His
785                 790                 795                 800
Leu Gly Leu Asn Glu Asp Glu Gln Leu Pro Lys Val Pro Gln Thr Phe
                805                 810                 815
Glu Glu Trp Glu Glu Tyr Tyr Lys Asp Glu Phe Ile Met Met Ala Asp
            820                 825                 830
Ile Glu Glu Ser Glu Asn Ser Asp Glu Glu Lys Gly Pro Phe Leu Val
        835                 840                 845
Gly Pro Lys Gly Gly Phe Arg His Gln Met Glu Val Ser Tyr Lys Gln
    850                 855                 860
Tyr Lys Cys Glu His Asp Trp Asp Phe Thr Arg Thr Arg Val Lys Pro
865                 870                 875                 880
Cys Lys Arg Cys Leu Lys Thr Val Thr Lys Gly Gln Tyr Ile Tyr Cys
                885                 890                 895
Arg Thr Cys Lys Ile Thr Val Cys His Glu Cys Ser Glu Phe Cys Tyr
            900                 905                 910
Asn Ile Lys Ile Glu Gly Ala Glu Ala Val Lys Pro Pro Glu Lys Lys
        915                 920                 925
Ser Asn Tyr Glu Leu Leu Ala Lys Gln Leu Leu Ile Glu Asn Ser Lys
    930                 935                 940
Leu Lys Met Glu Lys Glu Ile Leu Ile Glu Glu Leu Asn Lys Glu Ile
945                 950                 955                 960
Lys Ala His Gln Glu Thr Lys Lys Gly Lys Glu Leu Tyr Ile Glu Glu
                965                 970                 975
Ala Ser Thr Glu Val Glu Asn Glu Ile Glu Thr Trp Lys Ser Arg Ala
            980                 985                 990
Glu Leu Phe Glu Ala Leu Tyr Asn Glu Glu Val Lys Lys Asn Lys Ala
        995                 1000                1005
Ser Thr Ser Ser Val Thr Glu Gly Met Tyr Gln Val Gln Ile Asp His
    1010                1015                1020
Leu Arg Lys Glu Leu Arg Glu Val Ala Thr Leu Glu Val Asn Lys
1025                1030                1035                1040
Val Glu Glu Ser Glu Glu Glu Ala Glu Glu Val Met Met Ala Ser Ala
                1045                1050                1055
Val Lys Asp Glu Met Tyr Arg Phe Pro Val Ile Ile Glu Val Pro Glu
            1060                1065                1070
Val Gly Lys Val Gln Leu Thr Ala Leu Leu Asp Thr Gly Ala Thr Arg
        1075                1080                1085
Ser Cys Ile Asn Gln Val Phe Ile Glu Glu Lys Phe Leu Gln Pro Thr
    1090                1095                1100
Lys Phe Lys Val Lys Ile His Gly Val Asn Ser Val Thr Lys Leu Asp
1105                1110                1115                1120
Arg Gln Val Lys Asp Gly Ala Lys Leu Trp Ala Gly Glu Asn Trp Phe
                1125                1130                1135
Arg Leu Pro Ile Thr Tyr Val Gly Pro Met Tyr Met Gly Glu Lys Thr
            1140                1145                1150
Gln Met Leu Ile Gly Cys Asn Phe Met Gln Ser Leu Ala Gly Gly Val
        1155                1160                1165
```

```
Arg Leu Glu Gly Arg Thr Val Thr Phe Tyr Lys Tyr Ile Ala Ser Ile
    1170                1175                1180

Lys Ala Asn Glu Tyr Leu Gln Ala Glu Ala Glu Ile Leu Val Ala
1185            1190                1195                1200

Thr Ser Glu Gln Glu Phe Ile Asn Arg Ser Phe Met Ser Lys Asn Lys
                1205                1210                1215

Arg Leu Leu Glu Glu Met Lys Glu Gln Gly Tyr Met Gly Glu Asp Thr
    1220                1225                1230

Leu Ala His Trp Asn Lys Asn Gln Ile Lys Cys Lys Ile Glu Leu Arg
        1235                1240                1245

Asn Pro Asp Leu Ile Ile Lys Asp Lys Pro Gln Thr Leu Leu Asn Ile
    1250                1255                1260

Gln Lys Lys Glu Ala Met Arg Lys His Ile Asp Ala Leu Leu Glu Arg
1265            1270                1275                1280

Lys Val Ile Arg Pro Ser Lys Ser Pro His Arg Thr Asn Ala Phe Ile
                1285                1290                1295

Val Glu Ser Gly Thr Ser Ile Asp Pro Lys Thr Gly Lys Glu Ile Arg
        1300                1305                1310

Gly Lys Pro Arg Leu Val Phe Asn Tyr Lys Arg Leu Asn Asp Asn Thr
    1315                1320                1325

Trp Pro Asp Gln Tyr Ser Leu Pro Gly Ile Asn Ala Leu Leu Lys Asn
    1330                1335                1340

Val Ala Arg Ala Lys Ile Phe Ser Lys Phe Asp Leu Lys Ser Gly Phe
1345            1350                1355                1360

His Gln Val Ala Met Asp Glu Glu Ser Ile Pro Leu Thr Ala Phe Ser
                1365                1370                1375

Ala Tyr Asn Glu Leu Tyr Glu Trp Leu Val Met Pro Phe Gly Leu Lys
        1380                1385                1390

Asn Ala Pro Ala Ile Phe Gln Arg Lys Met Asp Gln Cys Phe Arg Gly
    1395                1400                1405

Thr Glu Gly Phe Ile Ala Val Tyr Ile Asp Asp Ile Leu Val Phe Ser
    1410                1415                1420

Glu Asp Glu Glu Gln His Ala Glu His Leu Trp Lys Met Leu Gln Ile
1425            1430                1435                1440

Cys Lys Arg Asn Gly Leu Ile Leu Ser Pro Ser Lys Tyr Lys Ile Gly
                1445                1450                1455

Val Lys Lys Val Asp Phe Leu Gly Ser Thr Ile Gly Asp Asn Gln Leu
        1460                1465                1470

Ala Val Gln Glu His Ile Ile Lys Lys Ile Ala Glu Phe Asp Asp Glu
        1475                1480                1485

Lys Leu Lys Thr Lys Glu Gly Leu Lys Ser Trp Leu Ala Thr Leu Asn
    1490                1495                1500

Tyr Ala Arg Asn His Ile Lys Asp Met Gly Lys Leu Leu Gly Pro Leu
1505            1510                1515                1520

Tyr Pro Lys Thr Ser Glu Lys Gly Glu Arg Arg Leu Asn Ser Glu Asp
                1525                1530                1535

Trp Lys Leu Ile Asn Arg Ile Lys Thr Met Val Arg Thr Leu Pro Asn
        1540                1545                1550

Leu Thr Ile Pro Pro Glu Asp Ala Tyr Ile Ile Glu Thr Asp Ala
    1555                1560                1565

Cys Ala Thr Gly Trp Gly Ala Val Cys Lys Trp Lys Lys Asn Lys Ala
    1570                1575                1580

Asp Pro Arg Asn Thr Glu Gln Ile Cys Arg Tyr Ala Ser Gly Lys Phe
```

-continued

```
      1585                1590                1595                1600

Asp Lys Pro Lys Gly Thr Cys Asp Ala Glu Ile Tyr Gly Val Met Asn
                1605                1610                1615

Gly Leu Glu Lys Met Arg Leu Phe Tyr Leu Asp Lys Arg Glu Ile Thr
            1620                1625                1630

Val Arg Thr Asp Ser Ser Ala Ile Glu Arg Phe Tyr Asn Lys Ser Ala
        1635                1640                1645

Glu His Lys Pro Ser Glu Ile Arg Trp Ile Arg Phe Met Asp Tyr Ile
    1650                1655                1660

Thr Gly Ala Gly Pro Glu Ile Val Ile Glu His Ile Lys Gly Lys Ser
1665                1670                1675                1680

Asn Gly Leu Ala Asp Ile Leu Ser Arg Leu Lys Ala Lys Leu Ala Gln
                1685                1690                1695

Asn Glu Pro Thr Glu Glu Met Ile Leu Leu Thr Gln Ala Ile Arg Glu
            1700                1705                1710

Val Ile Pro Tyr Pro Asp His Pro Tyr Thr Glu Gln Leu Arg Glu Trp
        1715                1720                1725

Gly Asn Lys Ile Leu Asp Pro Phe Pro Thr Phe Lys Asp Met Phe
    1730                1735                1740

Glu Arg Thr Glu Gln Ala Phe Met Leu Thr Glu Glu Pro Val Leu Leu
1745                1750                1755                1760

Cys Ala Cys Arg Lys Pro Ala Ile Gln Leu Val Ser Arg Thr Ser Ala
                1765                1770                1775

Asn Pro Gly Arg Lys Phe Phe Lys Cys Ala Met Asn Lys Cys His Cys
            1780                1785                1790

Trp Tyr Trp Ala Asp Leu Ile Glu Glu His Ile Gln Asp Arg Ile Asp
        1795                1800                1805

Glu Phe Leu Lys Asn Leu Glu Val Leu Lys Thr Gly Gly Val Gln Thr
    1810                1815                1820

Met Glu Glu Glu Leu Met Lys Glu Val Thr Lys Leu Lys Ile Glu Glu
1825                1830                1835                1840

Gln Glu Phe Glu Glu Tyr Gln Ala Thr Pro Arg Ala Met Ser Pro Val
                1845                1850                1855

Ala Ala Glu Asp Val Leu Asp Leu Gln Asp Val Ser Asn Asp Asp
            1860                1865                1870
```

<210> SEQ ID NO 2
<211> LENGTH: 7568
<212> TYPE: DNA
<213> ORGANISM: Sugarcane bacilliform virus

<400> SEQUENCE: 2

| | | | | |
|---|---|---|---|---|
| tggtatcaga gcgaggtatg atttctgtat ccgctatgtt ctaaatttct tagataaggg | 60 |
| gccaagggct ctgctgatga gtttaaggac aactacttgt gcaagttaca tagcatgata | 120 |
| cgtcgaaagg ctgaaaatat ccaaaatact gtctattgtt tggaaaacta ggttgttcta | 180 |
| ggggagaacg ttaatgaggg gtaagcttag ttcattctga aaatcaaggt ctgtgattgt | 240 |
| agttgagctc agtaattaag tgctgaagga agtaagatct aggtaggaca aaagtacccg | 300 |
| tcaaggcagg aggccgctaa ggggaaaaga gccagacgat caaagctttt tcagcacggt | 360 |
| tgttgagttt agctatcaag aaatagcctt gagactaaga ttcatcacta agaactgcct | 420 |
| actcaagcct ccctgaatcc gcctattagt acaaacgaga caacagtata aggagaaact | 480 |
| atatgcctgt aagacttaag tgcaaaagta acctctggaa ctgggtagaa gtctagagac | 540 |

-continued

| | |
|---|---|
| tctgaaagca tcccaaggta tcccttatct ccattagaac actgtgatac agttcttgta | 600 |
| tctaccttgc atgaaatctg aagccgagtg ggaaacacag tttaccgctt ggaagaattc | 660 |
| ccatatattc gaaaacgcta accaagagct tattcttgga acaaagatct ctaattctga | 720 |
| tttaaatcat aatctgcgta ctacttgcta tagagtagat cttggataca agttctgct | 780 |
| aacctcgcag cagaaggcgt tcgagcacag gaaggagcta ttctctgaag ggagaaagca | 840 |
| ccttgctgat caaagcagga agctacaact cgtagctgac aaagcggaac aatcgctgat | 900 |
| cattcagaag aacagcgtg cacgtctgaa aaggttgaa acggcctat cgaccctcag | 960 |
| tagggagatc cacgaccttc gtgtggaata cctgaagcgg aggcctttat caaaagaaga | 1020 |
| cgttgctgaa cttgtgctga caatctcaga gcagcccaag cttatcgaga agcagaccga | 1080 |
| gttgctcctc gagcaggtca agaagctggt ggagaccaca cgtagagaag ttgagacggt | 1140 |
| tcaccacatg gtgaaacgta tcagctgatg agtatcaacg aaccagcata cgcaaaggct | 1200 |
| ctcgagaaga ccaagaatat ccttggagag tcaggagaag gcttcgttgc aggaaacgca | 1260 |
| agcatcacaa cgcttaccaa gcagaataac ttaaccattg agttactgct tacccctgcac | 1320 |
| ggaaagatca agtctttgga ggacaaaatc caagacttga aggaagacct taccaagaag | 1380 |
| gcggacaagc ccagctcatc cgggctagac aagcaactcg acgacctcgc caagaggatc | 1440 |
| gaagggttga ggacaggagc agcacctgtc aaggtagttg aaaggggaa gctaaaagtt | 1500 |
| cacgctaatc cctttgaact cctgaggaag atccaatgac gcaaagagtc agaggtaccg | 1560 |
| gctccagtac catcacagaa gatggagcac tcttggatca ccagatccga gattacagaa | 1620 |
| gagcccagca tgcaaaacat gaggctcaga gaatcgcagg tcaagcactt gcttttctac | 1680 |
| gggttacctc agacgacccg agagagaaga ccctggagat gctcatgcag cctgatgtgg | 1740 |
| agctaaccag gagcatgaag aagagagcca gagctttccc agcagaagtt ctgtatggcc | 1800 |
| caagaagtga tgatattcat cacaaagtct ttcaagggac tctagccag gatatcctcc | 1860 |
| tgattgatga caatcagctt gatatgacct ttatcaagga ggaaacattc gagcaattgg | 1920 |
| agcaggcagg actccggtat attcatcccg gaatactagc tgttagaata cagcctctgc | 1980 |
| atccagactg gtcaggaaaa ctggttttca tagttttccg tgacatcaga gataacccac | 2040 |
| caagagtact tggagctatg gaaattgatc tgagcaaagg accacaaatg gtctatgtga | 2100 |
| tcaatagctt catgacaacg ataaaggatt tctttcatgg aatccagctt actgtcaagg | 2160 |
| tgaagggtta tgaaggttgg caaggagagg ccaacttaca cattgaaagg ttgataactg | 2220 |
| caagattgtc aaatacaacc aatgtgtatt tcaagtataa ggttgaagga gtggcgtctt | 2280 |
| ttatcaagac caaaggtata aaagctattg aagccactaa aaagagtgtg aagggcatca | 2340 |
| gaggaggaga atggaacatt ctcccatcaa agctagaggt agtcatgcaa cctaccaagg | 2400 |
| tgcagactac agaaaattat gatggcacaa catccttcag attcacaaat tatgaaggtg | 2460 |
| ccagttcttc aaagccagta gagcacaact cagatgatga ggcatatatg gcgctctttg | 2520 |
| aagaagaaga ggaagaggat gacatcactt tcctcaaccg aatcttatca agtactcta | 2580 |
| cgcagcaaaa ggtagtggga gaagaagaat ttccccaga agaagaccag attatttctg | 2640 |
| attttcttgg aaaaactgaa gaagcctacc ctgctgaaat tgaagaagag tacccagcgc | 2700 |
| taagaagact tgaacaactc atgaaaacaa aagttgttgt tcaagagatt gaagagccat | 2760 |
| cccagccagt tgaagctaag atgagtacaa gcactggatc atctgctatg atccctgcaa | 2820 |
| acatggacat ggatggaaac atgcctggct atgcaccagc acaagaagcc agaggatggg | 2880 |
| attcaggaga gactagcaga agaaactatg gtggacattc tagaaaatgg aaggatgaaa | 2940 |

-continued

```
gtcagttctt taatcttcca tctgccatgg caacatctgg agcgatgcta gttctcacaa   3000
tgggaaatta tgcaaaggag tttgatagat ggcagtctat caacacaaat ttattagcat   3060
cccagacatt tgagaatgca gaagacaaga tcaccaggat tgagaatctt cttggtgaaa   3120
cagaaaagct aatgttccag acctggagaa tggccttccc aacggccttt gaagcaatga   3180
aaactcaagc cacaggaaca aatggaacac agaatgtctt ctcacaaatg aagaggatat   3240
tgcttggaga ggttcctgaa caaggaacaa caaacactca agatgcagcc tacaagagga   3300
taaaatctct tgtctgccaa gaaatgacat atccagcaat catgagatat ctagttggat   3360
atagaaattt ggctgccaga tcaggaagag cttgggttaa caatgagtta actgatgaat   3420
tcttcaccaa gctaccagga aaattaggag accgggtaaa agaagctttc aagaagaagt   3480
atcccggagt tgaaaggcat gtcccagcgg ccacaagatt tacatatgat tacctggaag   3540
aaatttgtac agaaaacaac ttccagaagc aactcagaag cctgaatttc tgcaaaggct   3600
tcccagtggt caatcctgtt ggaacaagga aatatggaaa gaaatatggg acaagaaaag   3660
caagatctta cagaggcaag ccacacaagt ctcatgtaag aatagagaag aagaaatatc   3720
tgcagcaaag agagaagaaa tgcagatgct atgtctgtgg ttcaccagat cacctgatga   3780
aggactgcaa aagtcctatg aagagacaag aaagggtgaa cttggcaaat gaattggata   3840
tcccagatgg ctatgaccta gtctctgttg gatatgatga atcagacatc gatgaaatct   3900
attcagtatc agaaaatgaa gaatgtcagg cacatctagg cctgaatgaa gatgaacagc   3960
taccaaaggt tcctcaaacc tttgaagaat gggaagagta ctacaaagat gagttcatca   4020
tgatggctga tattgaagaa agtgagaatt cagatgaaga aaagggtccg ttccttgtag   4080
gaccaaaagg aggtttcagg caccaaatgg aagtctcata caagcaatac aagtgtgagc   4140
atgattggga ttttacaaga acaagggtaa aaccttgcaa aagatgcctg aagacagtga   4200
caaaggggca gtacatatac tgcaggacat gcaagatcac agtttgtcat gaatgctcag   4260
aattctgcta caatatcaaa atcgagggag cagaagcagt caagcccccca gaaaagaagt   4320
caaactatga gctgctggcc aaacagttgc tgattgaaaa tagcaagctc aaaatggaga   4380
aagagattct tattgaagaa ctcaacaagg aaataaaagc tcatcaagaa acaaagaaag   4440
gaaaagagct ttacattgaa gaagcttcca cggaggtgga aaatgaaatt gaaacatgga   4500
agagtagggc agaattgttt gaagccctat acaatgaaga agtaaagaag aataaagcca   4560
gtacatccag tgtgacagaa gggatgtacc aagtccagat cgaccaccta agaaaagaac   4620
tcagggaagt tgaggcaacc cttgaggtaa acaaggtcga agaatctgaa gaagaagctg   4680
aagaagtgat gatggcttca gcagttaaag atgagatgta cagattccca gtgatcatag   4740
aagttccaga agttggaaag gtacaactca cagctctctt ggatacaggt gcaacaaggt   4800
cctgtatcaa ccaagtattc attgaagaga agtttctcca acccacgaag ttcaaagtca   4860
agatacatgg ggtaaactca gtaacaaagc ttgaccgaca agtcaaagat ggtgcaaagc   4920
tttgggcagg agaaaattgg ttcagactcc cgatcacata tgttggacca atgtacatgg   4980
gagaaaagac gcagatgctc ataggatgca attttatgca atccttagca ggaggagttc   5040
ggctggaagg aagaacagtg accttctaca aatacattgc cagtattaag gcaaatgagt   5100
acttgcaagc cgaagcagag gaaattcttg ttgctacctc agaacaagaa tttatcaaca   5160
gaagtttcat gagcaagaac aagaggcttc ttgaggagat gaaggagcaa ggatatatgg   5220
gtgaagatac cttggctcac tggaacaaga atcagatcaa gtgcaagatt gaattgagaa   5280
```

```
acccagatct gattattaaa gacaagcctc agacactatt gaacattcag aagaaagaag    5340
caatgaggaa gcatattgat gctctcctag aaagaaaagt catcaggcct tcgaagagtc    5400
ctcacaggac caatgcattc attgtggaat cgggtacatc aattgacccg aagactggaa    5460
aggaaatcag aggaaaacca agactggttt tcaattacaa gaggctaaat gacaacacat    5520
ggccggatca atattcattg cccggaatca atgctctact aaaaaatgtt gcaagagcaa    5580
agatcttctc aaagtttgat ttgaagagcg ggtttcatca agtcgccatg gatgaagaaa    5640
gtattccatt aacagcattt tcagcataca atgagctgta tgaatggctg gtcatgccat    5700
ttggattaaa gaatgcacca gcaatcttcc agagaaaaat ggaccagtgt tcagaggaa     5760
cagaagggtt catagctgtg tatattgatg acatattggt tttctcggag gacgaagaac    5820
agcatgctga acatctgtgg aagatgcttc aaatctgcaa aaggaatgga ctaatcttga    5880
gtccgtcaaa gtacaagata ggagttaaga aggtggattt cttgggaagc acaattggtg    5940
acaaccaatt agcagtccaa gaacatatta ttaagaagat tgcagaattt gatgacgaga    6000
agttgaagac aaaagaaggt cttaaatcct ggctagcaac actgaactat gccagaaacc    6060
acatcaaaga tatgggcaag cttcttggcc cattatatcc aaagacctca gagaaaggtg    6120
agcgaaggct caattcagaa gattggaagc tgatcaatag gatcaagaca atggtgagaa    6180
cgcttccaaa tctcactatt ccaccagaag atgcatacat tatcattgaa acagatgcat    6240
gtgcaactgg atggggagca gtatgcaagt ggaagaaaaa caaggcagac ccaagaaata    6300
cagagcaaat ctgtaggtat gccagtgaa aatttgataa gccaaaagga acctgtgatg     6360
cagaaatcta tggggttatg aatggcttag aaaagatgag attgttctac ttggacaaaa    6420
gagagatcac agtcagaact gacagtagtg caatcgaaag gttctacaac aagagtgctg    6480
aacacaagcc ttctgagatc agatggatca ggttcatgga ctacatcact ggtgcaggac    6540
cagagatagt cattgaacac ataaaaggga agagcaatgg tttagctgac atcttgtcca    6600
ggctcaaagc caaattagct cagaatgaac caacggaaga gatgatcctg cttacacaag    6660
ccataaggga agtaattcct tatccagatc atccatacac tgagcaactc agagaatggg    6720
gaaacaaaat tctggatcca ttccccacat tcaagaagga catgttcgaa agaacagagc    6780
aagcttttat gctaacagag gaaccagttc tactctgtgc atgcaggaag cctgcaattc    6840
agttagtgtc cagaacatct gccaacccag aaggaaatt cttcaagtgc gcaatgaaca     6900
aatgccattg ctggtactgg gcagatctca ttgaagaaca cattcaagac agaattgatg    6960
aatttctcaa gaatcttgaa gttctgaaga ccggtggcgt gcaaacaatg gaggaggaac    7020
ttatgaagga agtcaccaag ctgaagatag aagagcagga gttcgaggaa taccaggcca    7080
caccaagggc tatgtcgcca gtagccgcag aagatgtgct agatctccaa gacgtaagca    7140
atgacgattg aggaggcatt gacgtcaggg atgaccgcag cggagagtac tgggcccatt    7200
cagtggatgc tccactgagt tgtattattg tgtgcttttc ggacaagtgt gctgtccact    7260
ttcttttggc acctgtgcca ctttattcct tgtctgccac gatgcctttg cttagcttgt    7320
aagcaaggat cgcagtgcgt gtgtgacacc acccccttc cgacgctctg cctatataag     7380
gcaccgtctg taagctctta cgatcatcgg tagttcacca catgatcatt tgagcaagtt    7440
tgcttgaata aaagaactat cattccgcat acctgatcct atagtcctag cttgagaaca    7500
agagcgaagt ctatagttga gatcctaaga gaaactcgag gttttcgggg tttcctgggc    7560
gcgttccc                                                             7568
```

<210> SEQ ID NO 3
<211> LENGTH: 1207
<212> TYPE: DNA
<213> ORGANISM: Sugarcane bacilliform virus

<400> SEQUENCE: 3

| | | | | | |
|---|---|---|---|---|---|
| gaagttgaag | acaaaagaag | gtcttaaatc | ctggctagca | acactgaact | atgccagaaa | 60 |
| ccacatcaaa | gatatgggca | agcttcttgg | cccattatat | ccaagacct | cagagaaagg | 120 |
| tgagcgaagg | ctcaattcag | aagattggaa | gctgatcaat | aggatcaaga | caatggtgag | 180 |
| aacgcttcca | aatctcacta | ttccaccaga | agatgcatac | attatcattg | aaacagatgc | 240 |
| atgtgcaact | ggatggggag | cagtatgcaa | gtggaagaaa | aacaaggcag | acccaagaaa | 300 |
| tacagagcaa | atctgtaggt | atgccagtgg | aaaatttgat | aagccaaaag | gaacctgtga | 360 |
| tgcagaaatc | tatggggtta | tgaatggctt | agaaagatg | agattgttct | acttggacaa | 420 |
| aagagagatc | acagtcagaa | ctgacagtag | tgcaatcgaa | aggttctaca | acaagagtgc | 480 |
| tgaacacaag | ccttctgaga | tcagatggat | caggttcatg | gactacatca | ctggtgcagg | 540 |
| accagagata | gtcattgaac | acataaaagg | gaagagcaat | ggtttagctg | acatcttgtc | 600 |
| caggctcaaa | gccaaattag | ctcagaatga | accaacggaa | gagatgatcc | tgcttacaca | 660 |
| agccataagg | gaagtaattc | cttatccaga | tcatccatac | actgagcaac | tcagagaatg | 720 |
| gggaaacaaa | attctggatc | cattccccac | attcaagaag | gacatgttcg | aaagaacaga | 780 |
| gcaagctttt | atgctaacag | aggaaccagt | tctactctgt | gcatgcagga | agcctgcaat | 840 |
| tcagttagtg | tccagaacat | ctgccaaccc | aggaaggaaa | ttcttcaagt | gcgcaatgaa | 900 |
| caaatgccat | tgctggtact | gggcagatct | cattgaagaa | cacattcaag | acagaattga | 960 |
| tgaatttctc | aagaatcttg | aagttctgaa | gaccggtggc | gtgcaaacaa | tggaggagga | 1020 |
| acttatgaag | gaagtcacca | agctgaagat | agaagagcag | gagttcgagg | aataccaggc | 1080 |
| cacaccaagg | gctatgtcgc | cagtagccgc | agaagatgtg | ctagatctcc | aagacgtaag | 1140 |
| caatgacgat | tgaggaggca | ttgacgtcag | ggatgaccgc | agcggagagt | actgggccca | 1200 |
| ttcagtg | | | | | 1207 |

<210> SEQ ID NO 4
<211> LENGTH: 1301
<212> TYPE: DNA
<213> ORGANISM: Sugarcane bacilliform virus

<400> SEQUENCE: 4

| | | | | | |
|---|---|---|---|---|---|
| gaagttgaag | acaaaagaag | gtcttaaatc | ctggctagca | acactgaact | atgccagaaa | 60 |
| ccacatcaaa | gatatgggca | agcttcttgg | cccattatat | ccaagacct | cagagaaagg | 120 |
| tgagcgaagg | ctcaattcag | aagattggaa | gctgatcaat | aggatcaaga | caatggtgag | 180 |
| aacgcttcca | aatctcacta | ttccaccaga | agatgcatac | attatcattg | aaacagatgc | 240 |
| atgtgcaact | ggatggggag | cagtatgcaa | gtggaagaaa | aacaaggcag | acccaagaaa | 300 |
| tacagagcaa | atctgtaggt | atgccagtgg | aaaatttgat | aagccaaaag | gaacctgtga | 360 |
| tgcagaaatc | tatggggtta | tgaatggctt | agaaagatg | agattgttct | acttggacaa | 420 |
| aagagagatc | acagtcagaa | ctgacagtag | tgcaatcgaa | aggttctaca | acaagagtgc | 480 |
| tgaacacaag | ccttctgaga | tcagatggat | caggttcatg | gactacatca | ctggtgcagg | 540 |
| accagagata | gtcattgaac | acataaaagg | gaagagcaat | ggtttagctg | acatcttgtc | 600 |
| caggctcaaa | gccaaattag | ctcagaatga | accaacggaa | gagatgatcc | tgcttacaca | 660 |

-continued

```
agccataagg gaagtaattc cttatccaga tcatccatac actgagcaac tcagagaatg        720
gggaaacaaa attctggatc cattccccac attcaagaag acatgttcg aaagaacaga         780 gcaagctttt atgctaacag aggaaccagt tctactctgt gcatgcagga agcctgcaat        840
tcagttagtg tccagaacat ctgccaaccc aggaaggaaa ttcttcaagt gcgcaatgaa        900
caaatgccat tgctggtact gggcagatct cattgaagaa cacattcaag acagaattga       960
tgaatttctc aagaatcttg aagttctgaa gaccggtggc gtgcaaacaa tggaggagga       1020
acttatgaag gaagtcacca agctgaagat agaagagcag gagttcgagg aataccaggc      1080
cacaccaagg gctatgtcgc cagtagccgc agaagatgtg ctagatctcc aagacgtaag       1140
caatgacgat tgaggaggca ttgacgtcag ggatgaccgc agcggagagt actgggccca      1200
ttcagtggat gctccactga gttgtattat tgtgtgcttt tcggacaagt gtgctgtcca       1260
cttctttttg gcacctgtgc cactttattc cttgtctgcc a                          1301
```

<210> SEQ ID NO 5
<211> LENGTH: 1422
<212> TYPE: DNA
<213> ORGANISM: Sugarcane bacilliform virus

<400> SEQUENCE: 5

```
gaagttgaag acaaaagaag gtcttaaatc ctggctagca acactgaact atgccagaaa       60
ccacatcaaa gatatgggca agcttcttgg cccattatat ccaaagacct cagagaaagg      120
tgagcgaagg ctcaattcag aagattggaa gctgatcaat aggatcaaga caatggtgag      180
aacgcttcca aatctcacta ttccaccaga agatgcatac attatcattg aaacagatgc      240
atgtgcaact ggatgtggag cagtatgcaa gtggaagaaa acaaggcag acccaagaaa       300 tacagagcaa atctgtaggt atgccagtgg aaaatttgat aagccaaaag gaacctgtga     360
tgcagaaatc tatggggtta tgaatggctt agaaaagatg agattgttct acttggacaa     420
aagagagatc acagtcagaa ctgacagtag tgcaatcgaa aggttctaca caagagtgc      480 tgaacacaag ccttctgaga tcagatggat caggttcatg gactacatca ctggtgcagg     540
accagagata gtcattgaac ataaaaggg aagagcaat ggtttagctg acatcttgtc       600
caggctcaaa gccaaattag ctcagaatga accaacggaa gagatgatcc tgcttacaca     660
agccataagg gaagtaattc cttatccaga tcatccatac actgagcaac tcagagaatg      720
gggaaacaaa attctggatc cattccccac attcaagaag acatgttcg aaagaacaga       780 gcaagctttt atgctaacag aggaaccagt tctactctgt gcatgcagga agcctgcaat      840
tcagttagtg tccagaacat ctgccaaccc aggaaggaaa ttcttcaagt gcgcaatgaa      900
caaatgccat tgctggtact gggcagatct cattgaagaa cacattcaag acagaattga    960
tgaatttctc aagaatcttg aagttctgaa gaccggtggc gtgcaaacaa tggaggagga   1020
acttatgaag gaagtcacca agctgaagat agaagagcag gagttcgagg aataccaggc  1080
cacaccaagg gctatgtcgc cagtagccgc agaagatgtg ctagatctcc aagacgtaag    1140
caatgacgat tgaggaggca ttgacgtcag ggatgaccgc agcggagagt actgggccca   1200
ttcagtggat gctccactga gttgtattat tgtgtgcttt tcggacaagt gtgctgtcca    1260
cttctttttg gcacctgtgc cactttattc cttgtctgcc acgatgcctt tgcttagctt    1320
gtaagcaagg atcgcagtgc gtgtgtgaca ccaccccct tccgacgctc tgcctatata    1380
aggcaccgtc tgtaagctct tacgatcatc ggtagttcac ca                      1422
```

```
<210> SEQ ID NO 6
<211> LENGTH: 32
<212> TYPE: DNA
<213> ORGANISM: Artificial Sequence
<220> FEATURE:
<223> OTHER INFORMATION: A primer

<400> SEQUENCE: 6
ctctagctgc aggaagttga agacaaaaga ag                                   32

<210> SEQ ID NO 7
<211> LENGTH: 31
<212> TYPE: DNA
<213> ORGANISM: Artificial Sequence
<220> FEATURE:
<223> OTHER INFORMATION: A primer

<400> SEQUENCE: 7
gtacgtaggc ctcactgaat gggcccagta c                                    31

<210> SEQ ID NO 8
<211> LENGTH: 31
<212> TYPE: DNA
<213> ORGANISM: Artificial Sequence
<220> FEATURE:
<223> OTHER INFORMATION: A primer

<400> SEQUENCE: 8
tacgataggc cttggcagac aaggaataaa g                                    31

<210> SEQ ID NO 9
<211> LENGTH: 31
<212> TYPE: DNA
<213> ORGANISM: Artificial Sequence
<220> FEATURE:
<223> OTHER INFORMATION: A primer

<400> SEQUENCE: 9
gcacgaaggc cttggtgaac taccgatgat c                                    31

<210> SEQ ID NO 10
<211> LENGTH: 25
<212> TYPE: DNA
<213> ORGANISM: Artificial Sequence
<220> FEATURE:
<223> OTHER INFORMATION: A primer

<400> SEQUENCE: 10
caggacggac catggatata tctcc                                           25
```